(12) United States Patent
Hansen

(10) Patent No.: US 7,272,510 B2
(45) Date of Patent: Sep. 18, 2007

(54) METHOD AND MEANS FOR CORRECTING MEASURING INSTRUMENTS

(75) Inventor: Per Waaben Hansen, Lyngby (DK)

(73) Assignee: Foss Analytical A/S, Hillerod (DK)

( * ) Notice: Subject to any disclaimer, the term of this patent is extended or adjusted under 35 U.S.C. 154(b) by 124 days.

(21) Appl. No.: 10/501,010

(22) PCT Filed: Dec. 11, 2002

(86) PCT No.: PCT/DK02/00839

§ 371 (c)(1),
(2), (4) Date: Jul. 8, 2004

(87) PCT Pub. No.: WO03/058214

PCT Pub. Date: Jul. 17, 2003

(65) Prior Publication Data

US 2005/0096853 A1 May 5, 2005

(30) Foreign Application Priority Data

Jan. 10, 2002 (DK) .................. PA 2002 00035

(51) Int. Cl.
*G01N 31/00* (2006.01)
(52) U.S. Cl. .................................. 702/28; 702/85
(58) Field of Classification Search ............... 702/28
See application file for complete search history.

(56) References Cited

U.S. PATENT DOCUMENTS

| | | | | |
|---|---|---|---|---|
| 4,168,431 A | * | 9/1979 | Henriksen | 378/53 |
| 4,866,644 A | * | 9/1989 | Shenk et al. | 356/319 |
| 4,893,253 A | * | 1/1990 | Lodder | 702/28 |
| 5,121,337 A | | 6/1992 | Brown | |

(Continued)

FOREIGN PATENT DOCUMENTS

EP     0 598 015 B1     8/1992

(Continued)

OTHER PUBLICATIONS

Yongdong Wang et al; Improvement of Multivariate Calibration through Instrument Standardization; Anal. Chem.. 1992, 64, 562-564.

(Continued)

*Primary Examiner*—John Barlow
*Assistant Examiner*—Jonathan Moffat
(74) *Attorney, Agent, or Firm*—Foley & Lardner LLP

(57) ABSTRACT

The invention relates to measuring instruments, preferably of the kind measuring absorbances, in an object, of electromagnetic radiation in at least two spectral ranges, such as IR instruments, and DXR, meaning Dual X-ray instruments, and more specifically to the determination of properties of food or feed, such as the fat content in milk or meat. The invention relates in particular to a method of providing a correction for a slave instrument of the kind measuring properties of an object by exposing the object to electromagnetic radiation, in particular X-rays, in at least two spectral ranges and obtaining one or more object responses thereto. The responses obtained being preferably based on detecting attenuation and/or reflection and/or scatter of the electromagnetic radiation in/from the object by use of one or more detectors and are obtained in a form where they express properties of the object either directly or via a transformation.

60 Claims, 13 Drawing Sheets

U.S. PATENT DOCUMENTS

| | | | |
|---|---|---|---|
| 5,252,829 A | 10/1993 | Nygaard et al. | |
| 5,357,336 A | 10/1994 | Ruhl, Jr. et al. | |
| 5,456,677 A | 10/1995 | Spector | |
| 5,459,677 A * | 10/1995 | Kowalski et al. | 703/2 |
| 5,559,728 A | 9/1996 | Kowalski et al. | |
| 5,933,792 A | 8/1999 | Andersen et al. | |
| 6,049,762 A | 4/2000 | Ganz et al. | |
| 6,128,544 A | 10/2000 | Alain et al. | |
| 6,138,082 A | 10/2000 | Wang et al. | |

FOREIGN PATENT DOCUMENTS

| | | |
|---|---|---|
| SE | 9203711 | 12/1992 |
| WO | WO 93/06460 | 4/1993 |
| WO | WO 95/16201 | 6/1995 |
| WO | WO 98/43070 | 10/1998 |
| WO | WO 01 29557 A | 4/2001 |

OTHER PUBLICATIONS

Yongdong Wang et al; Standardization of Second-Order Instruments; Anal. Chem. 1993, 65, 1174-1180.

Yondong Wang et al; Multivariate Instrument Standardization; Anal. Chem. 1991, 63, 2750-2756.

Partial Least Squares (PLS), StatSoft, Inc.; Aug. 13, 2001; 1-12.

* cited by examiner

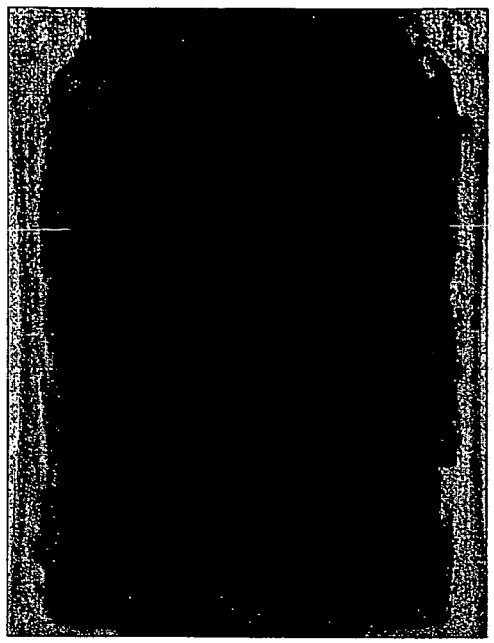
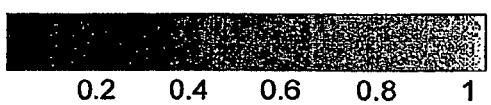
0.2   0.4   0.6   0.8   1
Low energy transmission
Fig. 5
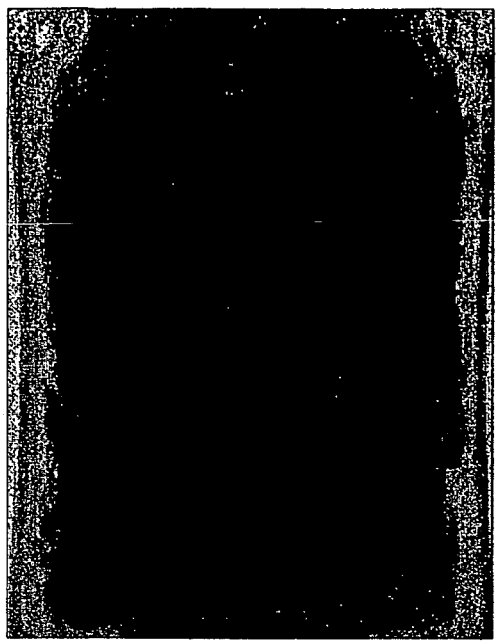
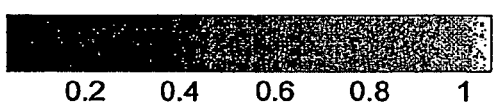
0.2   0.4   0.6   0.8   1
High energy transmission
Fig. 6

Areal density (g/cm²)

Fat content (%)

"Fat map" (g/cm²)

FIG. 12
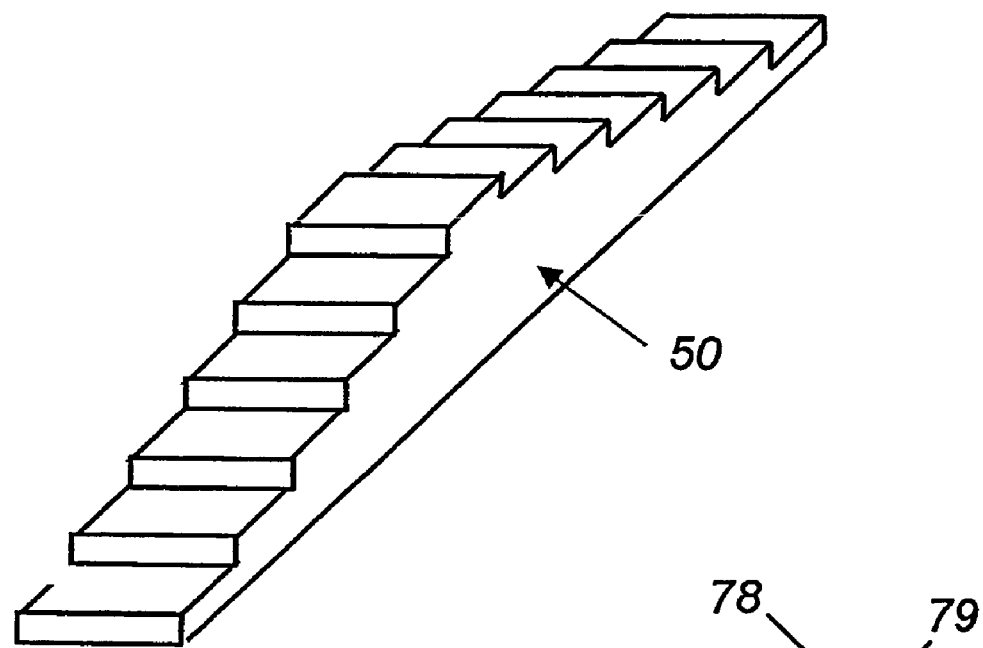
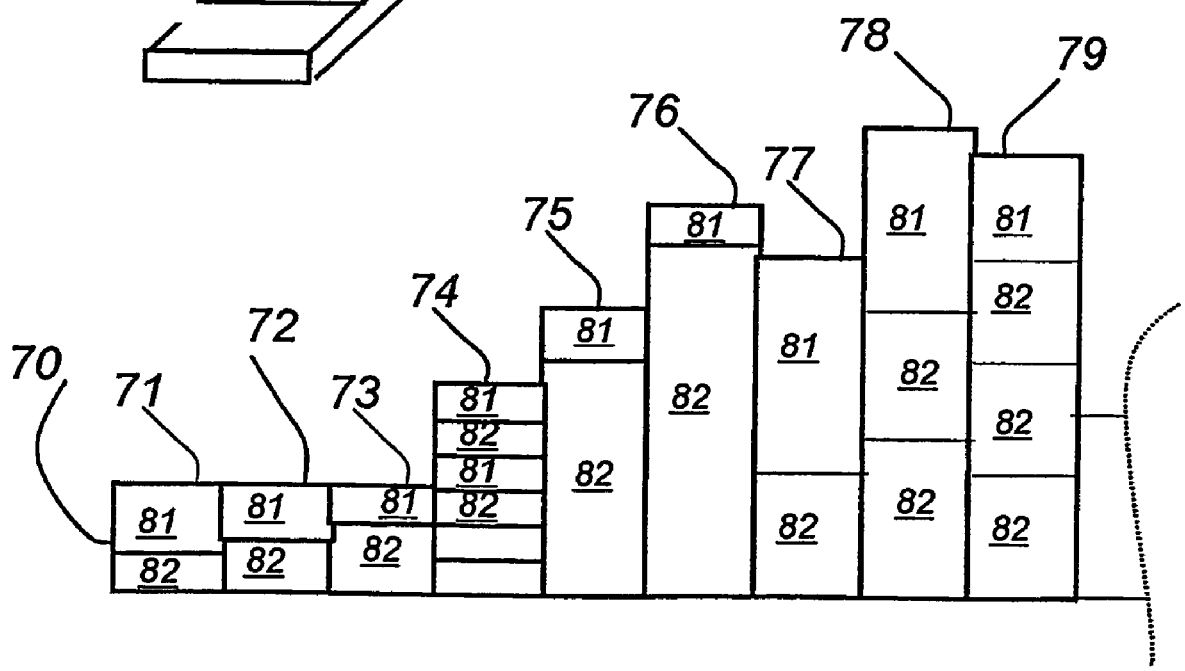
FIG. 13

METHOD AND MEANS FOR CORRECTING MEASURING INSTRUMENTS

TECHNICAL FIELD

The present invention relates to measuring instruments, preferably of the kind measuring absorbances, in an object, of electromagnetic radiation in at least two spectral ranges, such as IR instruments, and DXR, meaning Dual X-ray instruments, and more specifically to the determination of properties of food or feed, such as the fat content in milk or meat.

BACKGROUND ART

Spectral instruments measuring e.g. infrared absorbances at several wavelengths in order to determine contents of specific components in a liquid such as milk are well known. Also X-ray analysis for determining the fat content of meat has been known for several years.

Typically such instruments apply regression analysis and multivariate calibration. Such analysis is known from e.g. the applicant's own PCT application No. WO 95/16201 disclosing the determination of extraneous water in milk samples using regression analysis and multivariate calibration. Further, the applicant's PCT application No. WO 98/43070 discloses measurement of acetone in milk using IR spectroscopy and multivariate calibration. The transfer of calibrations from one instrument to another has been discussed in U.S. Pat. No. 5,459,677 disclosing a "Calibration transfer for analytical instruments" and U.S. Pat. No. 5,559,728 disclosing "Calibration transfer for second order analytical instruments" and in the applicants U.S. Pat. No. 5,933,792 "Method of standardizing a spectrometer".

The applicant's WO 93/06460 discloses an infrared attenuation measuring system, including data processing based on multivariate calibration techniques, and the applicants U.S. Pat. No. 5,252,829 discloses a determination of urea in milk with improved accuracy using at least part of an infrared spectrum.

As disclosed in WO 01/29557 the properties a medium of food or feed, such as the fat content of meat, may be determined by use of dual X-ray absorptiometry, the medium being a raw material of food or feed, a product or intermediary product of food or feed, or a batch, sample or section of the same, the method comprising—scanning substantially all of the medium by X-ray beams having at least two energy levels, including a low level and a high level, —detecting the X-ray beams having passed through the medium for a plurality of areas (pixels) of the medium, —for each area calculating a value, $A_{low}$, representing the absorbance in the area of the medium at the low energy level, —for each area calculating a value, $A_{high}$ representing the absorbance in the area of the medium at the high energy level, further comprising for each area generating a plurality of values being products of the type $A_{low}^{n} * A_{high}^{m}$ wherein n and m are positive and/or negative integers or zero, and predicting the properties of the medium in this area by applying a multivariate calibration model to the plurality of values, wherein the calibration model defines relations between the plurality of values and properties of the medium. The advantage over the prior art is a more accurate determination of the properties, such as the fat content in the medium. The accuracy is specifically improved over the prior art when measuring layers of varying thickness. A further advantage is due to the fact that using the described method almost the whole product is measured instead of a sample thereof. Generally, extraction of a sample from—an inhomogeneous medium will introduce an error, because the sample may not be truly representative.

Preferably the calibration model is obtained by use of a multivariate regression method being included in the group comprising Principal Component Regression (PCR), Multiple Linear Regression (MLR), Partial Least Squares (PLS) regression, and Artificial Neural Networks (ANN).

A problem related to the prior art:

It is well known, that when a number of measurement instruments measure the same sample, each instrument will generally produce an instrument specific signal if no specific actions are taken to ensure that the signals produced by the instruments are identical for an identical sample. It is equally well known that it is desirable to be able to manufacture measuring instruments, which generate the same signal when exposed to the same sample.

Calibration of an instrument may remedy the problem. However the multivariate calibration, which is applied for the DXR analysis—as described above and in the published WO 01/29557—is a delicate matter requiring a number of known reference samples, which typically have to be analyzed by an officially recognized reference method. The provision of such analysis results of the delicate perishable calibration samples consisting of various mixed samples of meat and fat which have to be handled very carefully preferably as frozen items—are time consuming, tedious and expensive. Further the calculations required for providing the calibration are time consuming too and therefore, expensive. These drawbacks are emphasized when a large number of instruments must be calibrated. Furthermore, when such calibrations must be performed often, such as regularly due to drifting in the instruments, the calibration method may strongly influence the usefulness of the instruments in a negative manner.

Thus, an object of the present invention is to provide a method, which seeks to avoid the above-mentioned drawbacks. Accordingly it is an object to disclose a method and instruments enabling a single highly sophisticated calibration developed on a master instrument to be applied to all other instruments in a series of similar instruments.

More specifically it is an object to provide a method of adjustment or correction for a series of instruments in such a manner that they can use the same calibration.

The present invention is specifically useful to measurements on meat performed by use of Dual X-ray equipment designed for measuring fat and areal density in meat, as well as for detecting foreign bodies in a meat sample. Such a measurement should, in order to obtain an acceptable accuracy, detect X-ray attenuation at at least two X-ray energies. According to the particular aspect of the present invention an X-ray equipment comprising two X-ray sources and two X-ray detectors is used for measuring the absorbances. Measurements performed with such equipment have shown to be extremely delicate as the amount of X-rays absorbed by adipose (fat) and muscle tissue only differs slightly, thereby demanding extreme care in calibrating the instrument.

Thus, another object of the present invention is to provide a method, which ease set-up of an Dual-X-ray instrument so that it is capable of producing accurate measurement of fat and areal density in meat.

A further object is to allow for less restrictive instrument specifications, enabling the use of cheaper components having rather coarse tolerances, thereby reducing the total cost of the instrument.

DISCLOSURE OF THE INVENTION

In a first aspect of the present invention and in accordance with the objects of the invention, a method of providing a correcting for a slave instrument is suggested. The slave instrument is preferably of the kind measuring properties of an object by exposing the object to electromagnetic radiation, in particular X-rays, in at least two spectral ranges and obtaining one or more object responses thereto. The responses obtained being preferably based on detecting attenuation and/or reflection and/or scatter of the electromagnetic radiation in/from the object by use of one or more detectors and are obtained in a form where they express properties of the object either directly or via a transformation. The suggested method of correcting comprises:

obtaining, for a plurality of stable objects, a set of responses comprising one or more pair of related responses ($Q_{low}^s$ and $Q_{high}^s$) representing measurements in the at least two spectral ranges performed with the slave instrument and a set of responses, comprising one or more pair of related responses ($Q_{low}^m$ and $Q_{high}^m$) representing measurements in the at feast two spectral ranges performed with a master instrument, to each pair of related responses ($Q_{low}^s$ and $Q_{high}^s$) of the slave instrument corresponds a pair of related responses ($Q_{low}^m$ and $Q_{high}^m$) of the master instrument, and to each element in each pair of responses ($Q_{low}^s$ and $Q_{high}^s$) of the slave instrument corresponds an element in the corresponding pair of responses ($Q_{low}^m$ and $Q_{high}^m$) of the master instrument;

determining based on the sets of responses a correcting function being a functional relationship between a ratio of related responses of the master instrument and a sum of a plurality of terms, each term being a product of a correcting coefficient ($B_i$) and powers of related responses ($Q_{low}^s$ and $Q_{high}^s$) of the slave instrument, wherein each response being raised to a power being a positive or negative real number, or zero, thereby determining a first set of correcting coefficients ($B_0$; $B_1$; $B_2$ ... ) being multiplied on each of the terms; and storing the first set of correcting coefficients ($B_0$; $B_1$; $B_2$ ... ) in memory means included in or adapted for communication with data processing means included in or adapted for communication with the slave instrument.

Thanks to the provision of a correcting function, each instrument may be brought in a condition where each of them produces similar, such as identical, responses on identical objects. Thus, by utilizing the correcting functions the responses produced by slave instruments can be transformed into so-called standardized responses (or corrected responses) which when subjected to a calibration function depending on such standardized responses may provide the desired knowledge about the physical properties of a measured object.

Thus, while calibrations typically are tedious and expensive due to required chemical analysis of each object used in calibration and due to the high number of calibration objects needed for a satisfying calibration the correcting function may be obtained by use of a set of standardizing objects and a corresponding set of master responses preferably stored in any suitable medium, preferably a data memory, such as a disc delivered together with the set of standardizing objects or alternatively, a report written on paper.

Thereby, the most common job to be performed in connection with the present invention—is to achieve the same responses from the slave instrument, as would have been provided by the master instrument measuring the same object. This advantage is believed to be achieved by the present invention.

Thus, a calibration model will thereby be transferable between all standardized instruments, and the measurements, such as the X-ray determination of fat in meat, will be much easier to handle. The present method for correcting a slave instrument, such as a Dual-X-ray equipment, using a limited number of stable standardizing objects, is therefore considered very useful, and therefore also the method of obtaining a correcting function used in performing the correction.

Thanks to the saved set of correcting coefficients ($B_0$; $B_1$; $B_2$ ... ) the slave instrument inclusive the data processing means and stored programs will able to correct successive measurements on unknown objects providing substantially correct measurements results based on a calibration elaborated for a master instrument. This will be explained further in the detailed description.

The term response as used in this application means is always related to a detected signal and generally it will be related to at least two detected signals. Accordingly the response may be considered to be a mathematical transformation of a number of signals resulting from a detector. Such signals may typically be digital signals provided by an analogue to digital converter converting electrical signals, provided by the detectors, into digital representations of the signals. Thus, a response, for instance the intensity (I), is in this connection typically generated from a detector signal, typically being a voltage, current or digital representation, by applying a mathematical relation to the detector signal, such as $I=f(U)$ where f is a mathematical function and U is the voltage provided by a detector. In that sense all the responses considered are typically resulting from transformations of signals into responses. However, it is contemplated that the invention is applicable also in embodiments where the signals from the detectors, for instance a digital representation (e.g. as binary numbers), are used as responses as these signals, of course, express properties of the object.

Depending on the mode of employment of the invention, such responses are either used as they are provided, for instance by mathematical relations, or are transformed into transformed responses. Typical examples of responses are intensity, which may be considered as a response used as it is provided, transmittance through an object being—derived from measuring the intensity with and without the object, and therefore preferably being considered as a derived response, absorbance being derived from the transmittance, reflectance, which also may be considered as a response used as it is provided, and a Kubelka-Munk transformation being applied to the reflectance.

It should be noted that the designations "high" and "low" are used in general for designating two values where one of these is higher relatively to the other value. Furthermore, two or more separate sources may be utilized in connection with the present invention as well a combination of one source and two filters emitting a low and a high energy beam.

The method according to the present invention comprises preferably the step of initially at a manufactures site measuring the plurality of stable objects on a master instrument, thereby obtaining the set of responses representing measurements performed with the master instrument ($Q_{low}^m$ and $Q_{high}^m$), storing the set of responses ($Q_{low}^m$ and $Q_{high}^m$) as a set of constant values in memory means, which is accessible from a slave instrument, when measuring the corresponding stable objects on a slave instrument in order to carry out a method of correcting according to the present invention.

Thereby, the responses needed for providing the correcting function is easy accessible and the workload connected with the method may be reduced.

Typically and preferably, the set of responses measured by the master instrument is stored in memory means included in or adapted for communication with data processing means included in or adapted for communication with the slave instrument.

The so-called "standardization" or correction is preferably based on a set of stable items which initially have been measured on a master instrument and all responses have been recorded on a recording medium such as a disc or ROM, which in the future follows the specific set of stable objects in view of the fact that such a set of stable objects typically is expensive a specific set of stable object could be used for many slave instruments, e.g. applied once a year during a maintenance visit by a service technician or when major changes are made to the instrument (such as a change of radiation source or a detector). In preferred embodiments such standardized responses and/or any specific calibration may be accessible through computer means of well-known art, e.g. through the Internet on a pay per use principle.

Typically and preferably, the determination of the correcting function being based on a regression method, which has proven to be a very efficient manner to obtain the correcting function. In preferred embodiments, the regression method is selected from the group consisting of principal component regression, multiple linear regression, partial least squares regression, and artificial neural networks. The partial least square method has proven to be especially useful.

It is generally preferred, that the correcting function comprises a plurality of terms of the following form $Q_{low}^{n1} * Q_{high}^{m1}$ wherein n1 and m2 are real numbers and/or integers, and n1 is positive. In accordance with preferred and practical very useful embodiments it is preferred that the correcting function comprises at least three of the following terms: $Q_{low}$, $Q_{high}$, $Q_{low}^2$, $Q_{high}^2$ and $Q_{low}/Q_{high}$. In order to achieve a higher accuracy in the correcting, more terms may preferably be added to the correcting function such that the correcting function comprises at least three of the following terms:

$Q_{low}*Q_{high}$; $Q_{low}^2*Q_{high}$; $Q_{low}*Q_{high}^2$; $Q_{low}^2/Q_{high}$; $Q_{low}/Q_{high}^2$; $Q_{low}^2/Q_{high}^2$; $Q_{low}^2/Q_{high}^2$.

In particular preferred embodiments of the invention, the correcting function is of the form:

$$\frac{Q_{low}^m}{Q_{high}^m} = B_1 Q_{low}^s + B_2 Q_{high}^s + B_3 Q_{low}^{s2} + B_4 Q_{high}^{s2} + B_5 Q_{low}^s Q_{high}^s + B_6 Q_{low}^{s2} Q_{high}^s + B_7 Q_{low}^s Q_{high}^{s2} + B_8 \frac{Q_{low}^{s2}}{Q_{high}^s} + B_9 \frac{Q_{low}^{s2}}{Q_{high}^s} + B_{10} \frac{Q_{low}^s}{Q_{high}^{s2}} + B_{11} \left[\frac{Q_{low}^s}{Q_{high}^s}\right]^2 + B_0$$

The above-defined method can be adequate for many cases. However, in a generalized version of the method the above-mentioned correcting function is accompanied by a further correcting function being determined based on the sets of responses and being a functional relationship between responses of the slave instrument ($Q_{low}^s$ or $Q_{high}^s$) and related responses ($Q_{low}^m$ or $Q_{high}^m$) of the master instrument. Thus, the method preferably comprises determination of a second set of correcting coefficients ($\alpha$; $\beta$).

Experience has shown that in some cases the further correcting function may improve the correction.

Preferably and typically, the further correcting function is a functional relationship between a high energy response of the slave instrument ($Q_{high}^s$) and the related high energy response ($Q_{high}^m$) of the master instrument. Furthermore, it is preferred that the further correcting function is determined by use of univariate linear regression.

In accordance with preferred embodiments of the present invention the further correcting function is preferably of the form $Q_{high}^m = \alpha \cdot Q_{high}^s + \beta$.

It is preferred that the set of responses for the master instrument and the set of responses for the slave instrument each comprises one pair of related responses for each stable object comprised in the plurality of stable objects.

In many practical implementations of the method the related responses are advantageously obtained based on measuring on objects being conveyed.

In cases where the detector or detectors used for providing the responses is/are sufficiently stable in time in the sense that it is not necessary to take measures to eliminate for instance detector drift in order to maintain the overall accuracy of the measurement, it might not be necessary to apply the method to any transformed responses. In such cases it is preferred that each of the responses (Q) is an intensity (I), if necessary corrected with respect to a variable parameter, e.g. dark current of the detectors. Thus, it might be preferred to correct the raw intensity with respect to the dark current in order to increase the stability of the responses by compensating for instability in the detector.

Such intensities are especially useful in situations where the intensities vary linearly or substantially linearly with physical properties reflected, which in particular is the situation where the measured absorption characteristics of an object varies over a narrow interval.

To compensate for further instabilities, e.g. due to radiation source instability, it is typically preferred that each of the responses is a transmittance (T) being derived from intensity as a ratio between intensity resulting from measuring on an object and reference intensity. Of course, such transmittances may also be preferred in general.

In preferred embodiments a linearization of transmittance is applied. In such and of course other embodiments as well, it is preferred that each of the responses is an absorbance being defined as the negative logarithm to a transmittance ($A = -\log(T)$) such as logarithm base 10, the natural logarithm, or any other logarithmic function.

In particular preferred embodiments of the present invention, the responses for both the master and the slave instruments are absorbances being determined by calculating $$A_{low} = -\log_{10}\left[\frac{I_{sample}(\text{low}) - I_{dark}(\text{low})}{I_{air}(\text{low}) - I_{dark}(\text{low})}\right] \text{ and}$$

$$A_{high} = -\log_{10}\left[\frac{I_{sample}(\text{high}) - I_{dark}(\text{high})}{I_{air}(\text{high}) - I_{dark}(\text{high})}\right]$$

wherein the intensities (I) are obtained in a measuring region of the master instrument respectively the slave instrument by:

exposing the object in the measuring region to low and high X-ray energies and detecting with detectors the intensities $I_{sample}$(low) and $I_{sample}$(high) respectively detecting the intensities $I_{dark}$(low) and $I_{dark}$(high) from said detectors when no radiation reaches them; and exposing said detectors to the low and high X-ray energies signals when no object is present in the measuring region and detecting $I_{air}$(low) and $I_{air}$(high).

In other preferred embodiments, each of the responses is selected to be a reflectance (R) expressing the reflectance from the surface of the object. The measured reflectance being useful in situations where the object to measured has such a nature that the properties to be measured is expressed by the reflectance of the object. It is contemplated that the reflectance covers surface reflectance of the object as well as reflectance in general of the object.

In preferred embodiments using reflectance it is preferred that the reflectance is linearized. In such embodiments the reflectance (R) is linearized, preferably by using the Kubelka-Munk transformation (K/S=(1–R)/2R).

The present invention relates in a second aspect to a method of correcting responses representing measurements performed with a slave instrument, said method comprising for an object determining based on measurements with the slave instrument a pair of related responses ($Q_{low}^s$ and $Q_{high}^s$), determining the ratio $[Q_{low}/Q_{high}]^{corr}$ by a correcting function being a functional relationship between a ratio of related responses of the master instrument and a sum of a plurality of terms, each term being a product of a correcting coefficient ($B_i$) and powers of related responses ($Q_{low}^s$ and $Q_{high}^s$) of the slave instrument wherein each response being raised to a power being a positive or negative real number, or zero, providing $Q_{high}^{corr}$ either by assuming that $Q_{high}^{corr}$ is substantially equal to $Q_{high}^s$ or by use of a further correcting function correlating $Q_{high}^{corr}$ with $Q_{high}^s$; and calculating $Q_{low}^{corr}$ as $Q_{high}^{corr} * [Q_{low}/Q_{high}]^{corr}$;

thereby providing a set of corrected responses.

Thus, in accordance with the invention, the method of correcting responses comprises preferably three operations, namely determination of a ratio of responses, determining one of the responses of the ratio of responses and finally multiplying said one of the responses on the ratio determined. It should be noted, that the assumption that $Q_{high}^{corr}$ is substantially equal to $Q_{high}^s$ can be construed as being a further correcting function (of the form $Q_{high}^{corr} = Q_{high}^s$) also, but is not termed so in order to ease the following discussion only.

When a further correcting function is utilised, this further correcting function is preferably of the form $Q_{high}^{corr} = \alpha \cdot Q_{high}^s + \beta$. It is contemplated that one or both of the coefficients ($\alpha$, $\beta$) and especially $\beta$ can be determined or selected to be equal to zero.

It is in general preferred that the correcting function comprises terms of the following form $Q_{low}^{n1} * Q_{high}^{m1}$ wherein n1 and m2 are real numbers and/or integers, and wherein n1 is positive. In accordance with preferred and practical very useful embodiments of the present invention it is preferred that the correcting function comprises the following terms: $Q_{low}$, $Q_{high}$, $Q_{low}^2$, $Q_{high}^2$ and $Q_{low}/Q_{high}$. In order to gain a higher accuracy in the correcting the correcting function may preferably comprise more terms such that the correcting function preferably comprises the following terms: $Q_{low}*Q_{high}$; $Q_{low}^2*Q_{high}$; $Q_{low}*Q_{high}^2$; $Q_{low}^2/Q_{high}$; $Q_{low}/Q_{high}^2$; $Q_{low}^2/Q_{high}^2$; $Q_{low}^2/Q_{high}^2$.

In particular preferred embodiments of the second aspect of the present invention the correcting function is of the form:

$$\left(\frac{Q_{low}}{Q_{high}}\right)^{corr} = $$
$$B_1 Q_{low}^s + B_2 Q_{high}^s + B_3 Q_{low}^{s2} + B_4 Q_{high}^{s2} + B_5 Q_{low}^s Q_{high}^s + B_6 Q_{low}^{s2} Q_{high}^{s2} +$$
$$B_7 Q_{low}^s Q_{high}^{s2} + B_8 \frac{Q_{low}^s}{Q_{high}^s} + B_9 \frac{Q_{low}^{s2}}{Q_{high}^s} + B_{10} \frac{Q_{low}^s}{Q_{high}^{s2}} + B_{11} \left[\frac{Q_{low}^s}{Q_{high}^s}\right]^2 + B_0$$

Wherein the B's preferably are constants being in general real numbers.

In preferred embodiments and as disclosed in relation to the first aspect of the present invention each of the responses (Q) is in some situations preferred to be an intensity (I), if necessary corrected with respect to the dark current of the detectors. Such intensity may advantageously be transformed into a transmittance (T) being derived from intensity as a ratio between intensity resulting from measuring on an object and a reference intensity.

In order to, for instance, linearize the responses, it might be preferred that each of responses is an absorbance being defined as the negative logarithm to a transmittance (A=–log(T)) such as logarithm base 10, the natural logarithm, or any other logarithmic function.

In particular preferred embodiments the responses are absorbances being determined by calculating $$A_{low} = -\log_{10}\left[\frac{I_{sample}(low) - I_{dark}(low)}{I_{air}(low) - I_{dark}(low)}\right] \text{ and}$$

$$A_{high} = -\log_{10}\left[\frac{I_{sample}(high) - I_{dark}(high)}{I_{air}(high) - I_{dark}(high)}\right]$$

wherein the intensities (I) are obtained in a measuring region of the slave instrument by:

exposing an object in the measuring region to low and high X-ray energies and detecting with detectors the intensities $I_{sample}$(low) and $I_{sample}$(high) respectively detecting with the detectors the intensities $I_{dark}$(low) and $I_{dark}$(high) from said detectors when no radiation reaches them; and exposing said detectors to the low and high X-ray energies signals when no object is present in the measuring region and detecting $I_{air}$(low) and $I_{air}$(high).

Also in this aspect of the present invention it may be preferred that each of the responses is a reflectance (R) expressing the reflectance from the surface of the object and the reflectance (R) may preferably and advantageously be linearized, preferably by using the Kubelka-Munk transformation (K/S=(1–R)/2R).

The correcting function and the further correcting function utilized in the second aspect of the present invention are preferably determined by the method according to the first aspect of the present invention.

The present invention relates in a third aspect to a method of determining a physical quantity for an object by a slave instrument. In this aspect the method comprises preferably determining for the object corrected high and low energy responses ($Q_{high}^{corr}$ and $Q_{low}^{corr}$) by utilizing the method according to the second aspect of the present invention, determining the physical quantity by applying on said corrected responses a calibrated functional relationship between $Q_{high}^{corr}$ and $Q_{low}^{corr}$ and a physical quantity.

In accordance with the third aspect, it is preferred that the calibrated functional relationship being a functional relationship between a physical quantity (such as the content of a specific constituent e.g. fat and meat), and a sum of a plurality of terms, each term being a product of a calibration coefficient ($B_i$) and powers of related responses ($Q_{low}^s$ and $Q_{high}^s$) wherein each response being raised to a power being a positive or negative real number, or zero.

In preferred embodiments of third aspect of the present invention, the calibrated functional relationship comprises terms being of the form: $Q_{low}^{n1}*Q_{high}^{m1}$ wherein n1 and m2 are real numbers and/or integers, and wherein n1 is positive. In order to for instance increase the accuracy of the calibrated functional relationship this relationship may preferably comprises terms being of the form: $Q_{low}$, $Q_{high}$, $Q_{low}^2$, $Q_{high}^2$ and $Q_{low}/Q_{high}$, or preferably comprises terms of the form: $Q_{low}*Q_{high}$; $Q_{low}^2*Q_{high}$; $Q_{low}*Q_{high}^2$; $Q_{low}^2/Q_{high}$; $Q_{low}/Q_{high}^2$; $Q_{low}^2/Q_{high}^2$; $Q_{low}^2/Q_{high}^2$.

In particular preferred embodiments according to the third aspect of the present invention the calibrated functional relationship is of the form:

$$F(Q) = B_1 Q_{low}^s + B_2 Q_{high}^s + B_3 Q_{low}^{s2} + B_4 Q_{high}^{s2} + B_5 Q_{low}^s Q_{high}^s + B_6 Q_{low}^{s2} Q_{high}^s + B_7 Q_{low}^s Q_{high}^{s2} + B_8 \frac{Q_{low}^s}{Q_{high}^s} + B_9 \frac{Q_{low}^{s2}}{Q_{high}^s} + B_{10} \frac{Q_{low}^s}{Q_{high}^{s2}} + B_{11} \left[\frac{Q_{low}^s}{Q_{high}^s}\right]^2 + B_0$$

It may furthermore be preferred that the calibration model is obtained by exposing the master instrument, such as an instrument having carried out the method according to the first aspect of the present invention, to a plurality of well-defined objects.

Typically and preferably, well-defined objects are defined in the sense that the physical properties of the objects have been established by a chemical process, such as an officially recognized reference method for the determination of the requested physical properties.

In preferred embodiments and as disclosed in relation to the other aspect of the present invention, each of the responses (Q) is preferably either:

an intensity (I), if necessary corrected with respect to dark current of the detectors;

a transmittance (T) being derived from intensity as a ratio between intensity resulting from measuring on an object and a reference intensity;

an absorbance being defined as the negative logarithm to a transmittance ($A=-\log(T)$) such as logarithm base 10, the natural logarithm, or any other logarithmic function; or a reflectance (R) expressing the reflectance from the surface of the object, the reflectance (R) is preferably linearized using the Kubelka-Munk transform ($K/S = (1-R)/2R$).

In particular preferred embodiments according to the third aspect of the present invention where the responses are absorbance, such absorbances are preferably being determined by calculating $$A_{low} = -\log_{10}\left[\frac{I_{sample}(\text{low}) - I_{dark}(\text{low})}{I_{air}(\text{low}) - I_{dark}(\text{low})}\right] \text{ and}$$

$$A_{high} = -\log_{10}\left[\frac{I_{sample}(\text{high}) - I_{dark}(\text{high})}{I_{air}(\text{high}) - I_{dark}(\text{high})}\right]$$

wherein the intensities (I) are obtained in a measuring region of the slave instrument by:

exposing an object in the measuring region to low and high X-ray energies and detecting with detectors the intensities $I_{sample}(\text{low})$ and $I_{sample}(\text{high})$ respectively detecting with the detectors the intensities $I_{dark}(\text{low})$ and $I_{dark}(\text{high})$ from said detectors when no radiation reaches them; and exposing said detectors to the low and high X-ray energies signals when no object is present in the measuring region and detecting $I_{air}(\text{low})$ and $I_{air}(\text{high})$.

In a fourth aspect the present invention relates to a method of using a slave instrument for determining physical quantities. Such physical quantities are for instance: preferably the fat content of an object, which object is for instance food or feed, and the quantities are preferably determined by use of dual X-ray radiation. In accordance herewith, the method comprises preferably:

scanning substantially all or all of the object by X-ray beams having at least two energy levels, including a low level and a level being higher relatively thereto, detecting the X-ray beams having passed through the object for a plurality of areas of the object;

for each area of the object determining the object's response ($Q_{low}$) at the low energy level and the object's response ($Q_{high}$) at the high energy level, correcting the responses so determined preferably by utilizing the correcting method according to the second aspect of the present invention, and determining the physical property preferably by utilizing the method according the third aspect of the present invention.

In a sixth aspect of the present invention, the invention relates to a data processing system for providing a correction for a slave instrument. Such a system utilizes preferably sets of responses being based on detecting attenuation and/or reflection and/or scatter of electromagnetic radiation, in particular X-ray, in/from a object exposed to said electromagnetic radiation in at least two spectral ranges. The set of responses comprises preferably one or more pair of related responses ($Q_{low}^s$ and $Q_{high}^s$) representing measurements performed with a slave instrument and a set of responses comprising one or more pair of related responses ($Q_{low}^m$ and $Q_{high}^m$ representing measurements performed with a master instrument. These responses being preferably obtained for a plurality of stable objects and to each pair of related responses of the slave instrument corresponds a pair of related responses of the master instrument, and to each element in each pair of responses of the slave instrument corresponds an element in the corresponding pair of responses of the master instrument.

In accordance with the sixth aspect the data processing system comprises preferably
- means for accessing memory means wherein the responses ($Q_{low}^m$ and $Q_{high}^m$) of the master instrument and/or the responses ($Q_{low}^s$ and $Q_{high}^s$) of the slave instrument are stored,
- means, such as processor means, for determining based on the sets of responses a correcting function being a functional relationship between a ratio of related responses of the master instrument and a sum of a plurality of terms, each term being a product of a correcting coefficient ($B_i$) and powers of related responses ($Q_{low}^s$ and $Q_{high}^s$) of the slave instrument wherein each response being raised to a power being a positive or negative real number, or zero, thereby determining a first set of correcting coefficients ($B_0$; $B_1$; $B_2$ . . . ) being multiplied on each of the terms,
- means for storing the first set of correction coefficients ($B_0$; $B_1$; $B_2$ . . . ).

Data processing systems of the sixth aspect of the invention comprise preferably means for determining a further correcting function being a functional relationship between a high energy response of the slave instrument ($Q_{high}^s$) and related high energy response ($Q_{high}^m$) of the master instrument, thereby enabling the system to determining a second set of correcting coefficients ($\alpha$; $\beta$).

In accordance with preferred embodiments of the data processing system according to the present invention, and as disclosed in connection with the other embodiments of the invention, it is preferred that each of the responses (Q) is either:
- an intensity (I), if necessary corrected with respect to dark current of the detectors;
- a transmittance (T) being derived from intensity as a ratio between intensity resulting from measuring on an object and reference intensity;
- an absorbance being defined as the negative logarithm to a transmittance (A=−log(T)) such as logarithm base 10, the natural logarithm, or any other logarithmic function; or
- a reflectance (R) expressing the reflectance from the surface of the object, the reflectance (R) is preferably linearized using the Kubelka-Munk transform (K/S=(1−R)/2R).

In particular preferred embodiments of the data processing system according to the present invention, in case the responses are absorbances, the absorbances being preferably determined by calculating $$A_{low} = -\log_{10}\left[\frac{I_{sample}(low) - I_{dark}(low)}{I_{air}(low) - I_{dark}(low)}\right] \text{ and}$$

$$A_{high} = -\log_{10}\left[\frac{I_{sample}(high) - I_{dark}(high)}{I_{air}(high) - I_{dark}(high)}\right]$$

wherein the intensities (I) are obtained in a measuring region of the slave instrument by:
- exposing an object in the measuring region to low and high X-ray energies and detecting with detectors the intensities $I_{sample}(low)$ and $I_{sample}(high)$ respectively
- detecting with the detectors the intensities $I_{dark}(low)$ and $I_{dark}(high)$ from said detectors when no radiation reaches them; and
- exposing said detectors to the low and high X-ray energies signals when no object is present in the measuring region and detecting $I_{air}(low)$ and $I_{air}(high)$.

In a seventh aspect, the invention relates to a correcting system comprising a slave instrument for obtaining responses and a data processing system for correcting the responses, the responses representing measurement performed with the slave instruments and the responses being based on detecting by the slave instrument attenuation and/or reflection and/or scatter of electromagnetic radiation, in particular X-ray, in/from an object exposed to said electromagnetic radiation in at least two spectral ranges, the set of responses comprises one or more pair of related responses ($Q_{low}^s$ and $Q_{high}^s$). In accordance herewith, the correcting system comprises preferably
- processor means for determining the one or more pair of related responses ($Q_{low}^s$ and $Q_{high}^s$) based on measurement on an object with the slave instrument,
- means comprising processor means adapted to perform a correction of responses by utilizing a correcting according to the second aspect of the present invention, said processor means comprises
  - means for accessing memory means storing a first set of correction coefficients ($B_0$; $B_1$; $B_2$ . . . )
  - processor means for determining the ratio $[Q_{low}/Q_{high}]^{corr}$ by the correcting function;
  - processor means for determining the corrected high energy response $Q_{high}^{corr}$ by the further correcting function; and
  - processor means for determining the corrected low energy response $Q_{low}^{corr}$ by multiplying $[Q_{low}/Q_{high}]^{corr}$ by $Q_{high}^{corr}$.

Also in this aspect of the invention, and as disclosed in connection with the other aspects of the invention, each of the responses (Q) is preferably either:
- an intensity (I), if necessary corrected with respect to dark current of the detectors;
- a transmittance (T) being derived from intensity as a ratio between intensity resulting from measuring on an object and reference intensity;
- an absorbance being defined as the negative logarithm to a transmittance (A=−log(T)) such as logarithm base 10, the natural logarithm, or any other logarithmic function; or
- a reflectance (R) expressing the reflectance from the surface of the object, the reflectance (R) is preferably linearized using the Kubelka-Munk transform (K/S=(1−R)/2R).

Preferably, the system according to the seventh aspect comprises storage means wherein a set of responses ($Q_{low}^m$ and $Q_{high}^m$) for a set of stable objects measured on a master instrument are stored and/or storage means wherein the first set of correction coefficients ($B_0$; $B_1$; $B_2$ . . . ) and/or the further correcting function is/are stored.

In an eighth aspect, the present invention relates to a dual X-ray instrument comprising a system according to the seventh aspect being adapted to carry out a method according to the first aspect of the invention.

In a ninth aspect, the present invention relates to a set of objects comprising one or more stable objects for, or used during, carrying out one or more of the methods according to the present invention. Preferably, each of such objects being characterized by being composed by at least two different chemical compositions which are substantially stable and each stable object is having response, such as absorbance, properties which are similar to the response, such as absorbance, properties of an object subjected to the method according to the second aspect of the present invention.

In accordance with the ninth aspect, it is preferred that for each of the stable objects a first member of the at least two different chemical compositions is one having X-ray response properties, such as absorbance properties, similar to adipose tissue, and a second member of the at least two different chemical compositions is one having X-ray response, such as absorbance, properties similar to muscle tissue.

In preferred embodiments of present invention, the set of stable objects comprises preferably a plurality of stable objects having varying thickness and/or areal density. The plurality of stable objects may advantageously be integrated into a single stepped item.

Preferably, each object comprised in the set of objects is stable in the sense that the X-ray response, such as absorption, properties of the object does not change more than 0.1%, such as no more than 0.01%, such as no more than 0,001% within at least 10 days, such as at least 1 month, preferably at least 1 year.

Preferably, the number of stable objects comprises in the set of stable objects are at least 8, such as at least 12, preferably at least 15, or even at least 20, such as at least 26.

In the following a particular preferred embodiment of the present invention will be presented as non-limiting example with reference to the accompanying figures, in which:

FIG. 5 shows a typical low energy X-ray transmission image of a meat sample as shown in FIG. 4.

FIG. 6 shows a typical high energy X-ray transmission image of the same meat sample.

FIG. 12 shows a second embodiment of an integrated standardization object

FIG. 13 shows a further embodiment of a number of steps and sections of an integrated standardization object.

DETAILED DESCRIPTION OF A PREFERRED EMBODIMENT OF THE PRESENT INVENTION

The present invention may be applied for instruments of the kind measuring absorbances, in a medium, of an electromagnetic radiation in at least two spectral ranges, which instrument is calibrated by use of a multivariate regression method. Such instruments may be spectral IR-instruments. However, the present invention has proved to be specifically useful for Dual X-ray analysis.

Description of the Equipment Used

Figure 1:
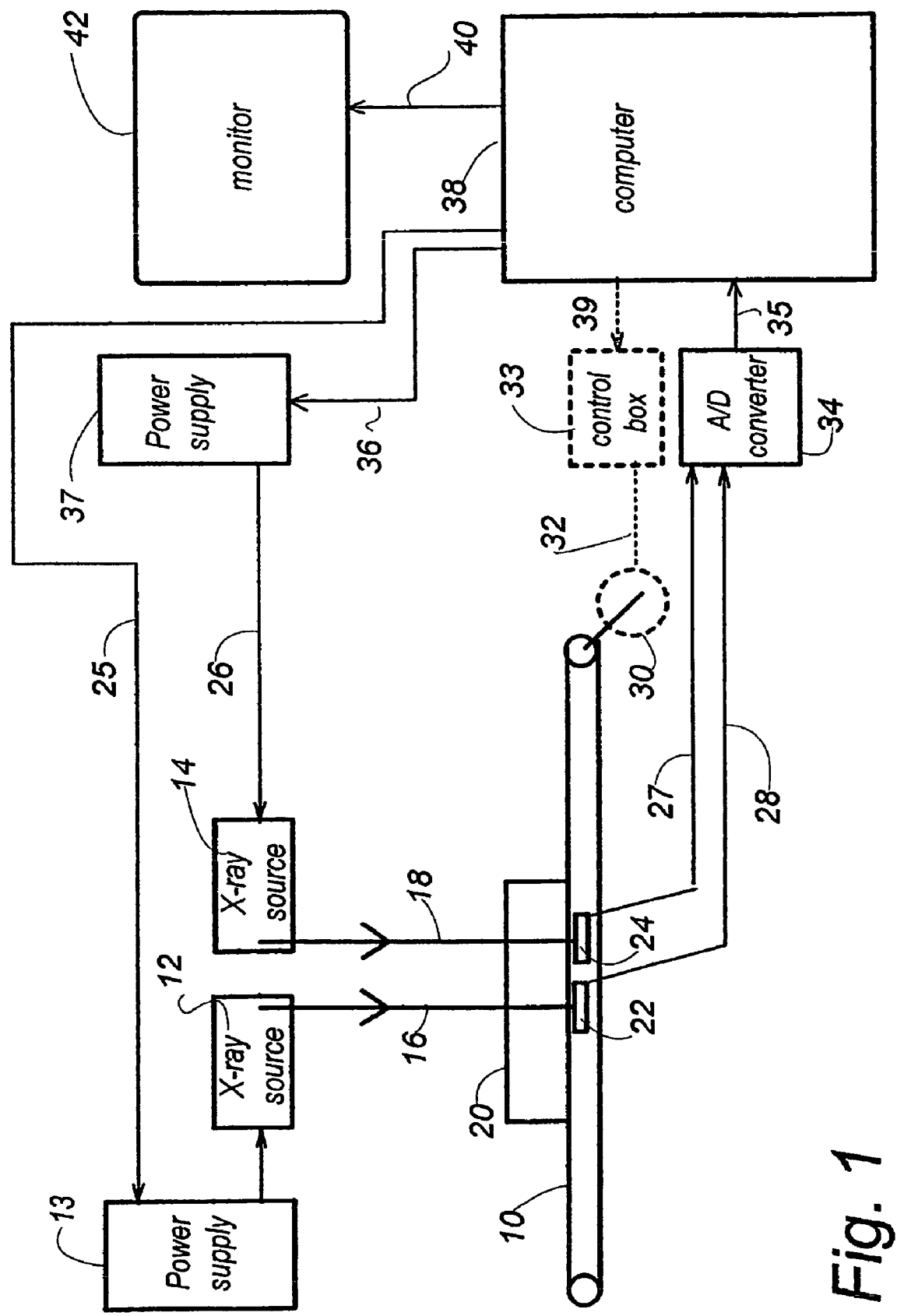
FIG. 1 shows a schematic diagram of an instrument incorporating means for carrying out a method according to the invention.
Figure 2:
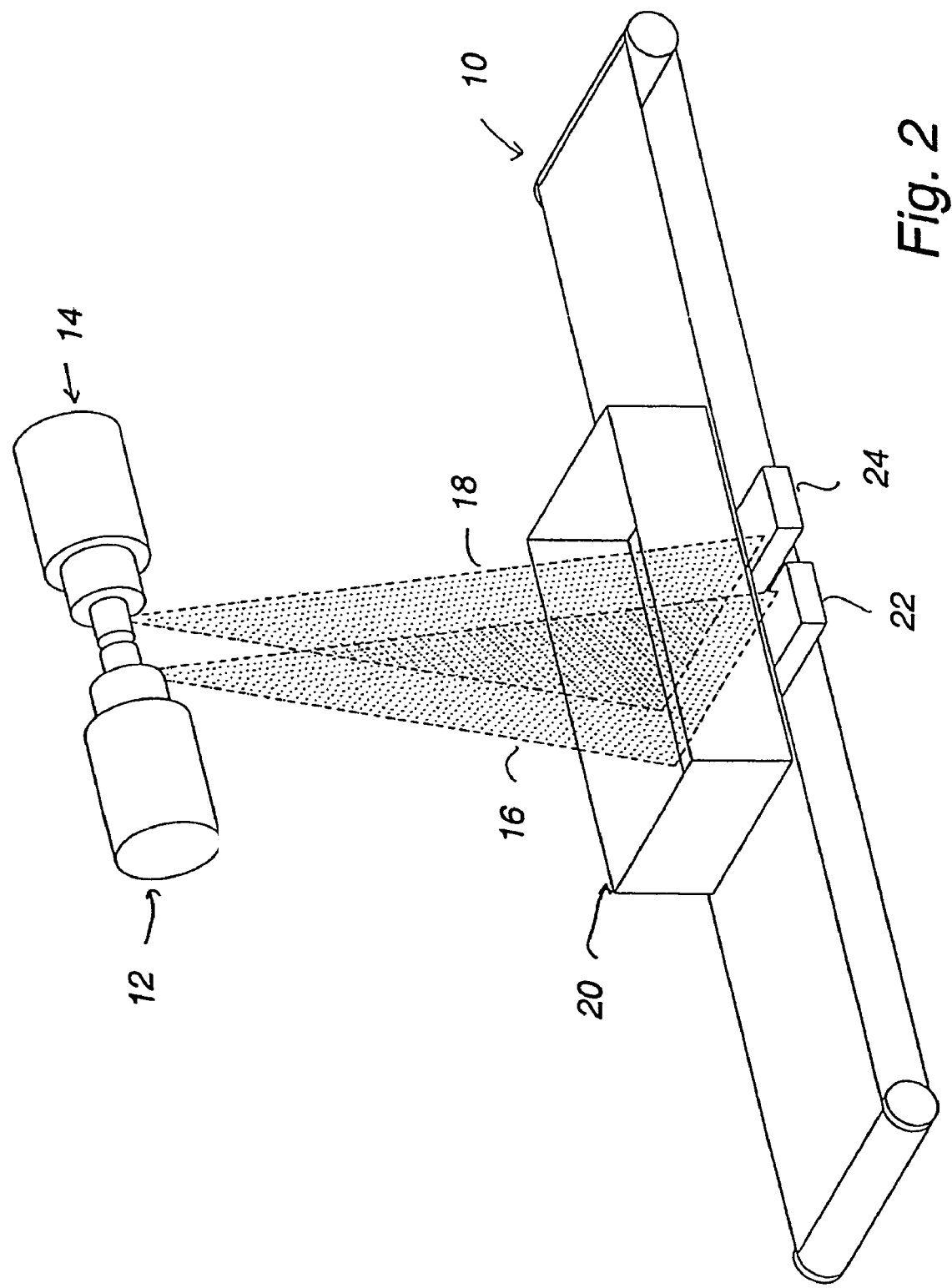
FIG. 2 shows a perspective view of an embodiment of the instrument in FIG. 1.

The following description discloses as an example a preferred embodiment of an instrument for which the present invention is specifically intended. The instrument uses two X-ray sources. The instrument is designed for being installed in relation to a production line in a slaughterhouse. FIG. 1 shows a schematic diagram of an embodiment of a measurement system for a determination of the fat content in meat. FIG. 2 is a perspective illustration of the presently preferred X-ray instrument. FIG. 2 shows only the active operating portions of the X-ray equipment. For purpose of clarity, all protective shielding or screening and all casings are deleted from the drawing. The equipment comprises or is located in close relation to a conveyor 10. Two X-ray sources 12, 14 are arranged above the conveyor 10. From the two sources 12, 14 X-ray beams 16, 18 are directed towards detectors 22, 24 arranged below the conveyor. The conveyor may be split into two separate conveyors spaced to allow free pass of the X-rays and to leave an open space for location of detectors 22, 24. Alternatively the conveyor belt should be made from a material showing a low absorbance of X-rays, e.g. polyurethane or polypropylene. The food or feed to be measured is arranged in an open container or box 20, preferably also composed by a material showing low absorbance of X-rays. Alternatively the medium such as a food product might be arranged directly on a conveyor belt. In a further alternative arrangement the X-ray sources could be located below the conveyor and the detectors above the conveyor.

The presently preferred equipment used in the present example consists of two constant potential X-ray sources 12, 14, one at low energy (e.g. 62 kV/5.5 mA) and another at high energy (e.g. 120 kV/3.0 mA), both with an appropriate filtration (e.g. using 0.25 and 1.75 mm of copper, respectively) narrowing the spectral range of the radiation emitted from the polychromatic sources. The two sources are spatially separated to avoid interference between them, i.e. to avoid that radiation from one source is detected as if it originated from the other. The radiation from either source is collimated by a lead collimator. In this way two fan-shaped beams of X-rays 16, 18 are directed through container 20 comprising a sample or batch of the food or feed product towards detectors 22, 24, e.g. Hamamatsu C 7390. Alternatively the meat lumps may be arranged loosely on a conveyor band.

Figure 3:
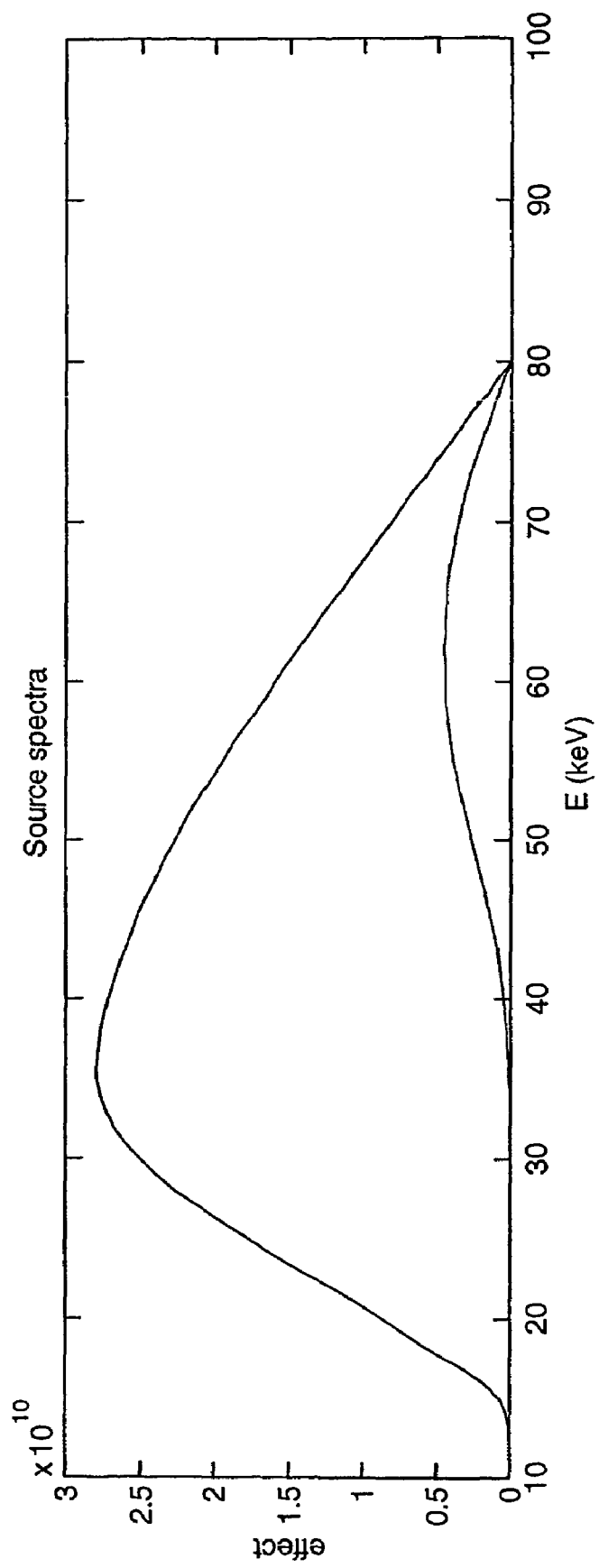
FIG. 3 shows an alternative spectrum of X-ray sources simulating two sources by use of one source and a combination of two filters.

Further, the two separate sources may be replaced by a combination of one source and two filters emitting a low energy and a high energy beam. The resulting source spectra are shown in FIG. 3. However the preferred embodiment applies two separate sources 12, 14 driven by separate power supplies 13, 37.

Each of the two X-ray sources 12, 14 is associated with an array of detectors 22, 24 covered with a scintillating layer converting the transmitted radiation into visible light that can be measured by the detectors 22, 24. The scintillating layer may consist of e.g. cadmium telluride, mercury iodide, cesium iodide (CsI), gadolinium oxysulphide (Gd$_2$O$_2$S), or yttrium oxysulphide (Y$_2$O$_2$S), and/or CdWO$_4$, preferably doped in order to reduce the after-glow effect. The pixels used in the presently preferred embodiment have the dimensions 1.6×1.3 mm$^2$ and are arranged as an array of 384 pixels with a pitch of 1.6 mm. These dimensions are only stated as an example. Other dimensions may be applied. The pixels convert the amount of transmitted light into analogue signals' that are passed through cables 27, 28 to an analogue-to-digital converter 34, which is connected through cable 35 to a computing means 38 capable of performing the successive calculations.

A monitor 42 may be connected through cable 40 to the computing means to show results or details of the operation. The computing means 38 may include means for controlling the supply of power through means 36, 37, 26 and 25, 13, 15 to the X ray sources 12, 14. The monitor 42 and the computing means 38 may comprise a Personal Computer, preferably including at least one Pentium processor and/or a number of digital signal processors.

The operational speed of the conveyor is preferably substantially constant. The items, motor 30; control box 33, and cables 32, 39, shown by phantom lines in FIG. 1, indicate that the operation of the conveyor optionally may be controlled by the computing means 38. The conveyor may include position measuring means, e.g. an encoder installed on a conveyor driving shaft. Alternative means may be a laser or radar detection or marks on the conveyor belt. It is essential to the present method that the data representing the two X-ray images can be synchronised. Such synchronisation may however be obtained in many ways, including mathematical post-processing of the images.

Figure 4:
FIG. 4 shows a typical meat sample in a plastic container.

Operation of the Instrument During a Normal Measurement:

A container 20, e.g. as shown in FIG. 4, comprising e.g. meat trimmings from a cutting section of the slaughterhouse, is received on the conveyor 10. The container is moved with a fairly constant speed of e.g. about 5-100 cm per second, such as 10-50 cm, e.g. 30 cm per second past the fan shaped beams 16, 18 and the arrays of detectors 22, 24 in a controlled manner in order to generate two "images" of the absorbances in the sample or batch, one at a low X-ray energy (shown in FIG. 5) and another at a high energy (shown in FIG. 6). All data representing the two images are stored in the computer 38.

Figure 14:
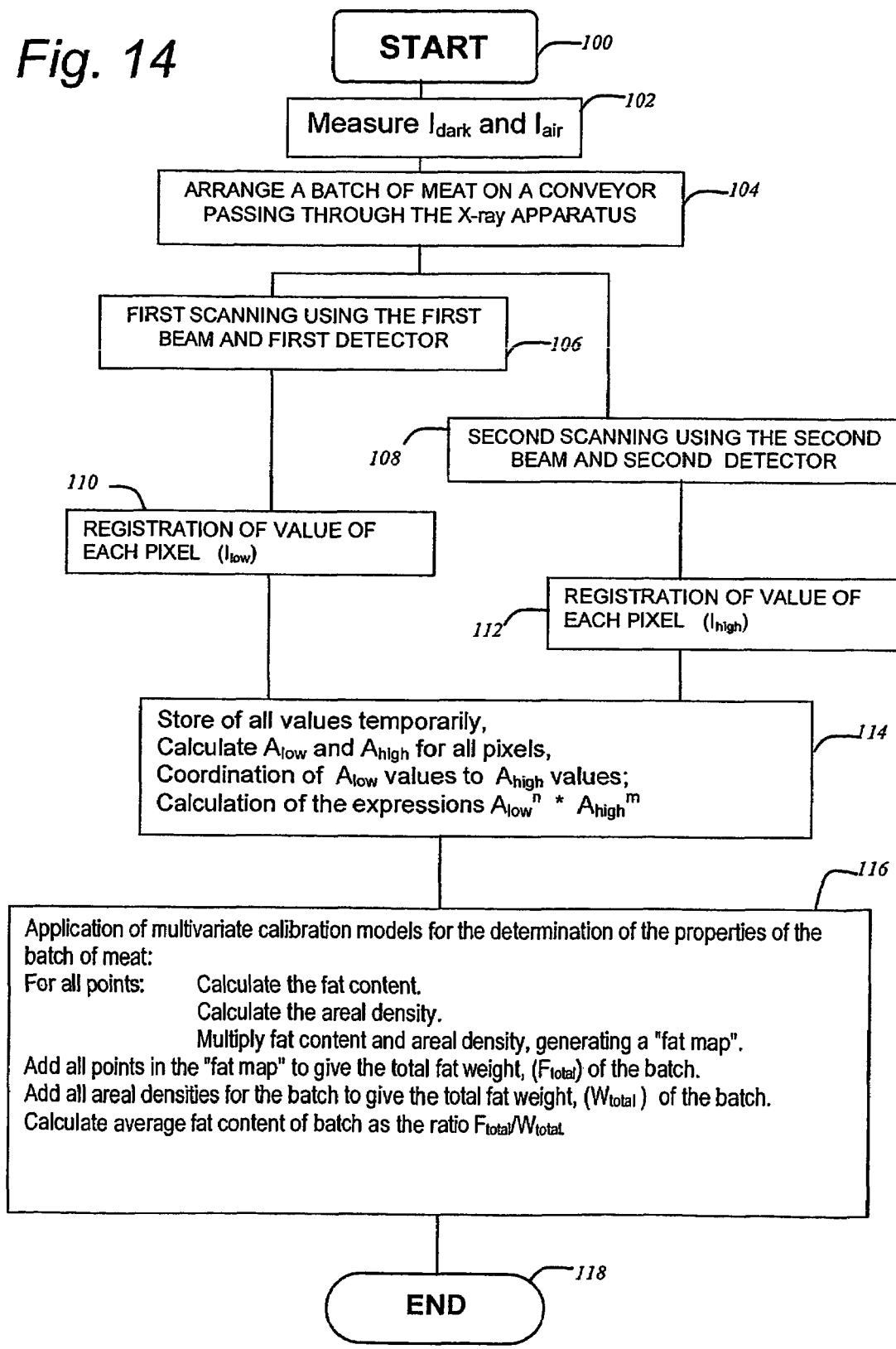
FIG. 14 shows a flow diagram illustrating the measuring process with a master instrument.

Treatment of the Collected Data from a Master Instrument:

FIG. 14 represents a flow chart illustrating the measurement and data treatment in a master instrument. The method is started in step 100 and ended in step 118 as shown in FIG. 14. As stated above, data representing two X-ray images of (FIGS. 5, 6) of each container (FIG. 4), comprising a batch of food or feed e.g. meat, are obtained (106, 108 in FIG. 14). The signals at the pixels are $I_{low}$ and $I_{high}$ at low and high X-ray energies, respectively, (110, 112 in FIG. 14). Furthermore, the so-called "dark signals" (i.e. the signal from the detectors when no radiation reaches them), $I_{dark}$ (low) and $I_{dark}$ (high), and the "air signals" (i.e. the signal from the detectors when no sample is present in the measure region), $I_{air}$(low) and $I_{air}$(high), are collected for each pixel at both X-ray energies (102 in FIG. 14). Preferably these data are collected repetitively in the intervals between the passage/passing of meat containers, i.e., the dark signals and air signals are measured repetitively, e.g. at regular intervals during a day to adjust for any drift of instrument performance.

Now referring to 114 in FIG. 14, these signals are transformed into absorbance units by using the following formulas:

$$A_{low} = -\log_{10}\left[\frac{I_{sample}(\text{low}) - I_{dark}(\text{low})}{I_{air}(\text{low}) - I_{dark}(\text{low})}\right] \quad (1a)$$

$$A_{high} = -\log_{10}\left[\frac{I_{sample}(\text{high}) - I_{dark}(\text{high})}{I_{air}(\text{high}) - I_{dark}(\text{high})}\right] \quad (1b)$$

Figure 7:
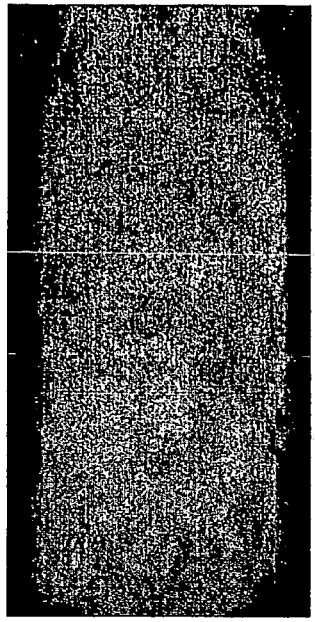
FIG. 7 is an image illustrating a calculated areal density for each individual pixel.
Figure 8:
FIG. 8 is an image illustrating a calculated fat content for each individual pixel.
Figure 9:
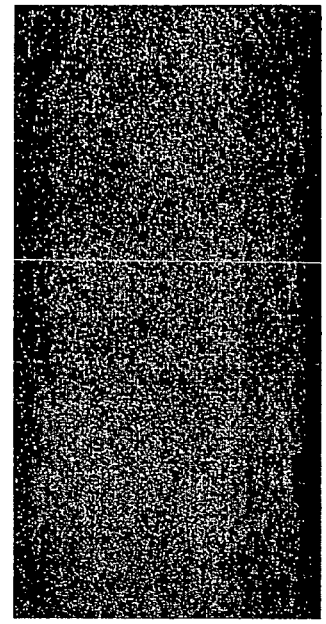
FIG. 9 is an image illustrating a calculated "fat map" for a meat sample of 36% fat.

If the instrument were a calibrated master instrument the areal density (FIG. 7) and fat content (FIGS. 8, 9) of the measured medium could now be calculated from these absorbances by use of the fat calibration as described in WO 01/29557 and shown schematically in box 116 in FIG. 14.

Description of the Method and Means According to the Present Invention:

A.: Description of the Standardisation Objects.

FIGS. 10-13 show various preferred embodiments of integrated standardization objects. The present method requires a plurality of stable objects, also called artificial samples due to the choice of material, which must be of a kind maintaining substantially constant absorption properties for a long period, such as several years, contrary to the medium, such as meat, for which this method is specifically—but not exclusively—intended. Preferably, the stable objects include a number of combinations of two X-ray absorbers, having absorption characteristics similar to the measured object, which in the present example is meat. Accordingly, in the present example, the two absorbers must behave like adipose and muscle tissue. In the presently preferred embodiment blocks of polymethyl methacrylate 81 (similar to adipose tissue) and "plastic water" 82 (a polymer with absorption characteristics similar to water, available from CIRS, Inc.) were used. Other alternatives, such as other purpose-made polymers made to resemble adipose and muscle tissue, could also be used. Liquid water (or ice) is another substance highly resembling muscle tissue.

In the present example twenty-six samples consisting of various combinations of these materials 81 82 were generated (areal densities ranging from approx. 1 to 22 g/cm$^2$) and used in the standardisation procedure.

Figure 10:
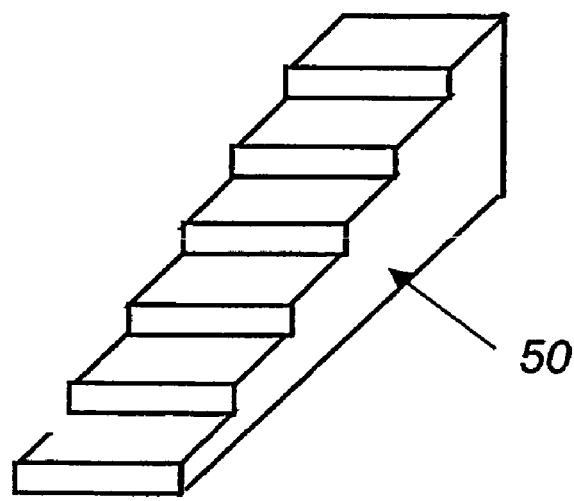
FIG. 10 shows an embodiment of an integrated standardization object.
Figure 11:
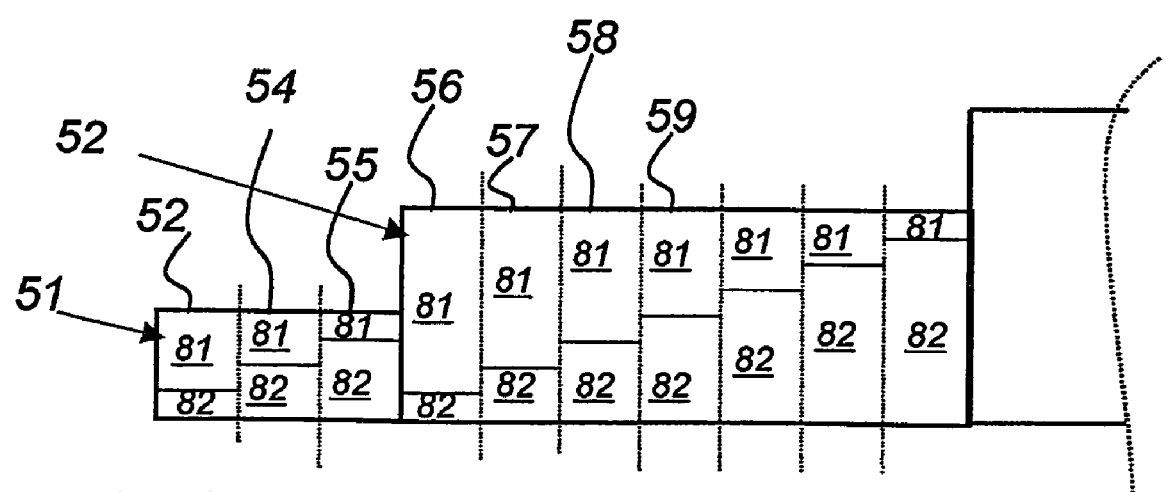
FIG. 11 shows an embodiment of individual steps of an integrated standardization object.

In order to make the standardization process easy to perform it is preferred that the whole number of different stable objects are integrated into a single item, e.g. a stepped item, e.g. like a staircase 50 as shown in FIGS. 10 and 12. As shown in FIGS. 11 and 13 each step 51, 52, 70, 71, . . . 79 may comprise one or two or an other plurality of different layers 81, 82 of e.g. the polymethyl methacrylate and "plastic water". Further each step 51, 52, 70 may comprise several sections 53, 54, 55, . . . 59, each having a specific combination of layers 81, 82 of various thickness. Preferably, the different combinations are chosen to provide a range of absorptions and properties, e.g. fat % similar to the absorptions and properties, e.g. fat %, in the media for which the instrument is intended.

Preferably, each section has the same size in the travel direction of the conveyor. Preferably, they also have the same size in a direction perpendicular to the travel direction and parallel to the conveyor belt. In other word the projection area on the generally horizontal plane of the conveyor belt of each section is the same in a preferred embodiment.

Each standardisation object is measured on a master instrument or standardized slave instrument. Preferably, each standardization object is marked by an identification code, such as a number. The measured absorbances and preferably the identification code are stored in a memory, which is accessible from a slave instrument, using the standardization object.

B Standardization of a Slave Instrument

The standardisation procedure requires a set of absorbances, $A_{low}^m$ and $A_{high}^m$, from a master instrument, and a set of corresponding absorbances, $A_{low}^s$ and $A_{high}^s$, from a slave instrument. These absorbances must originate from the same samples, e.g. a number of artificial standardisation samples, preferably being a standardization object as described above.

Figure 15:
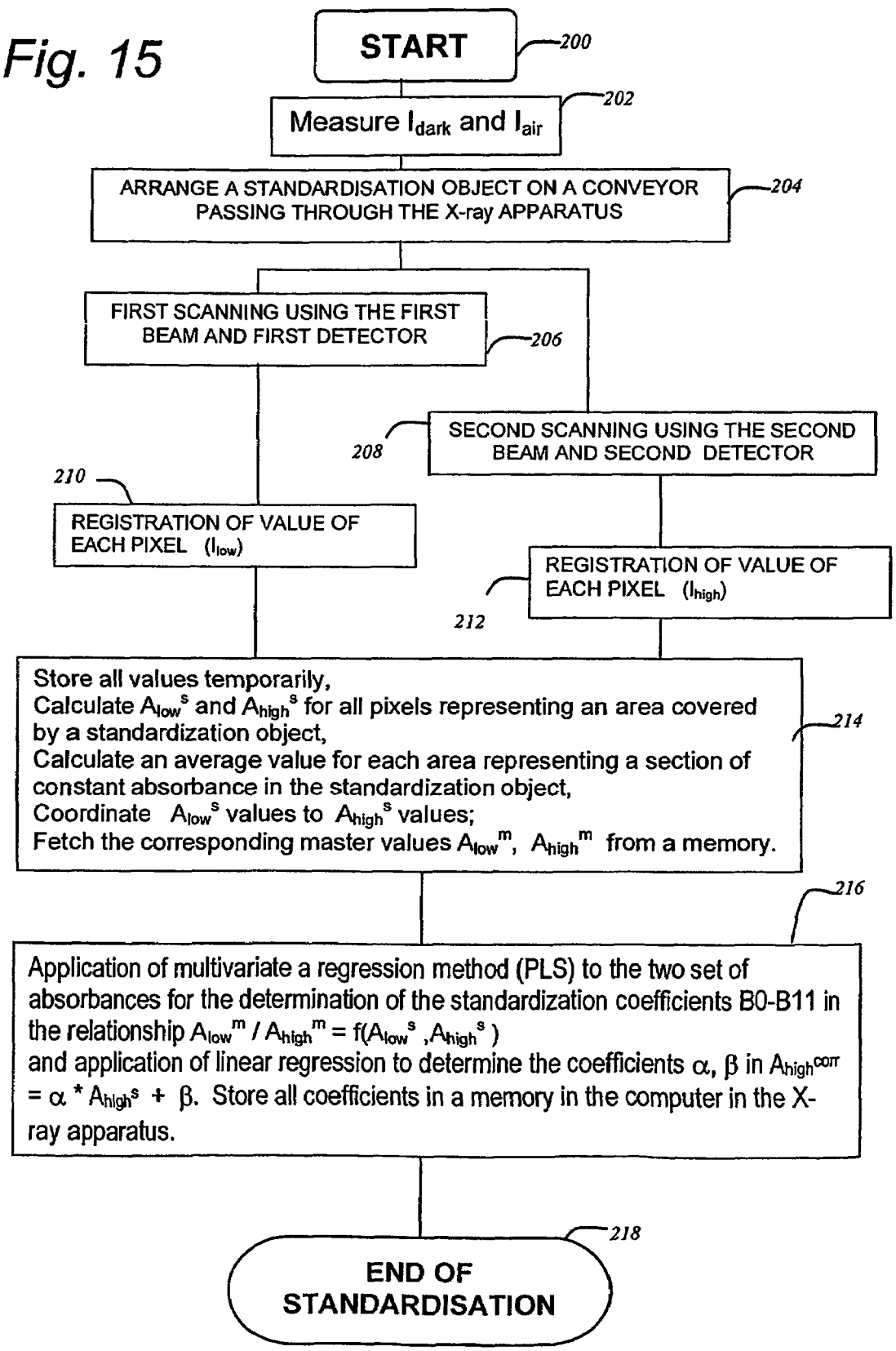
FIG. 15 shows a flow diagram illustrating the standardisation process.

A presently preferred method according to the invention is shown schematically in the diagram FIG. 15. In step 202 $I_{dark}$(low) and $I_{dark}$(high), and $I_{air}$(low) and $I_{air}$(high), are collected for each pixel at both X-ray energies. Preferably these data are collected repetitively in the intervals between the passage/passing of meat containers, i.e. the dark signals and air signals are measured repetitively, e.g. at regular intervals during a day to adjust for any drift of instrument performance.

In step 204 a standardization object 54 is arranged on the conveyor 10 (shown in FIGS. 1 and 2). The object is passed through the instrument in the same manner as an ordinary object to be measured. The steps 200, 202, 204, 206, 208, 210, 212, 218 are the same as corresponding reference numbers mentioned before regarding FIG. 14.

In the following step 214 average values $A_{low}^s$, $A_{high}^s$ are calculated for each section 53, 54, 55, . . . 59, of the standardization object 50 measured on the slave instrument. The values are calculated using formula (1a) and (1b). The high and low energy values are coordinated, i.e. the values belonging to the same section (53, 54, 55, . . . 59,) are matched. The corresponding values $A_{low}^m$, $A_{high}^m$, measured on a master instrument are read from a memory.

The following final steps listed in box 216 are then required to obtain an acceptable standardisation of the instruments:

1. The coefficients ($\alpha$ and $\beta$) in the equation describing the relationship between $A_{high}^m$ and $A_{high}^m$ are determined by univariate linear regression:

$$A_{high}^m = \alpha \cdot A_{high}^s + \beta$$

This step may in some cases be superfluous as a may be almost equal to 1 and $\beta$ close to zero.

2. A functional relationship, $f(A_{low}^s, A_{high}^s)$, between the $A_{low}^m/A_{high}^m$ ratio and various combinations of $A_{low}^s$ and $A_{high}^s$ is established. The following linear combination is preferred:

$$\frac{A_{low}^m}{A_{high}^m} = B_1 A_{low}^s + B_2 A_{high}^s + B_3 A_{low}^{s2} + B_4 A_{high}^{s2} +$$

$$B_5 A_{low}^s A_{high}^s + B_6 A_{low}^{s2} A_{high}^s + B_7 A_{low}^s A_{high}^{s2} + B_8 \frac{A_{low}^s}{A_{high}^s} +$$

$$B_9 \frac{A_{low}^{s2}}{A_{high}^s} + B_{10} \frac{A_{low}^s}{A_{high}^s} + B_{11} \left[\frac{A_{low}^s}{A_{high}^s}\right]^2 + B_0 = f(A_{low}^s, A_{high}^s)$$

The coefficients, $B_0$ to $B_{11}$, are be determined e.g. by using Partial Least Squares (PLS) regression. Alternatively other multivarialte regression methods may be used.

3. The coefficients, $\alpha$, $\beta$, and $B_0$ to $B_{11}$, are saved in the instrument. They are the instrument specific standardisation (correction) coefficients.

Figure 16:
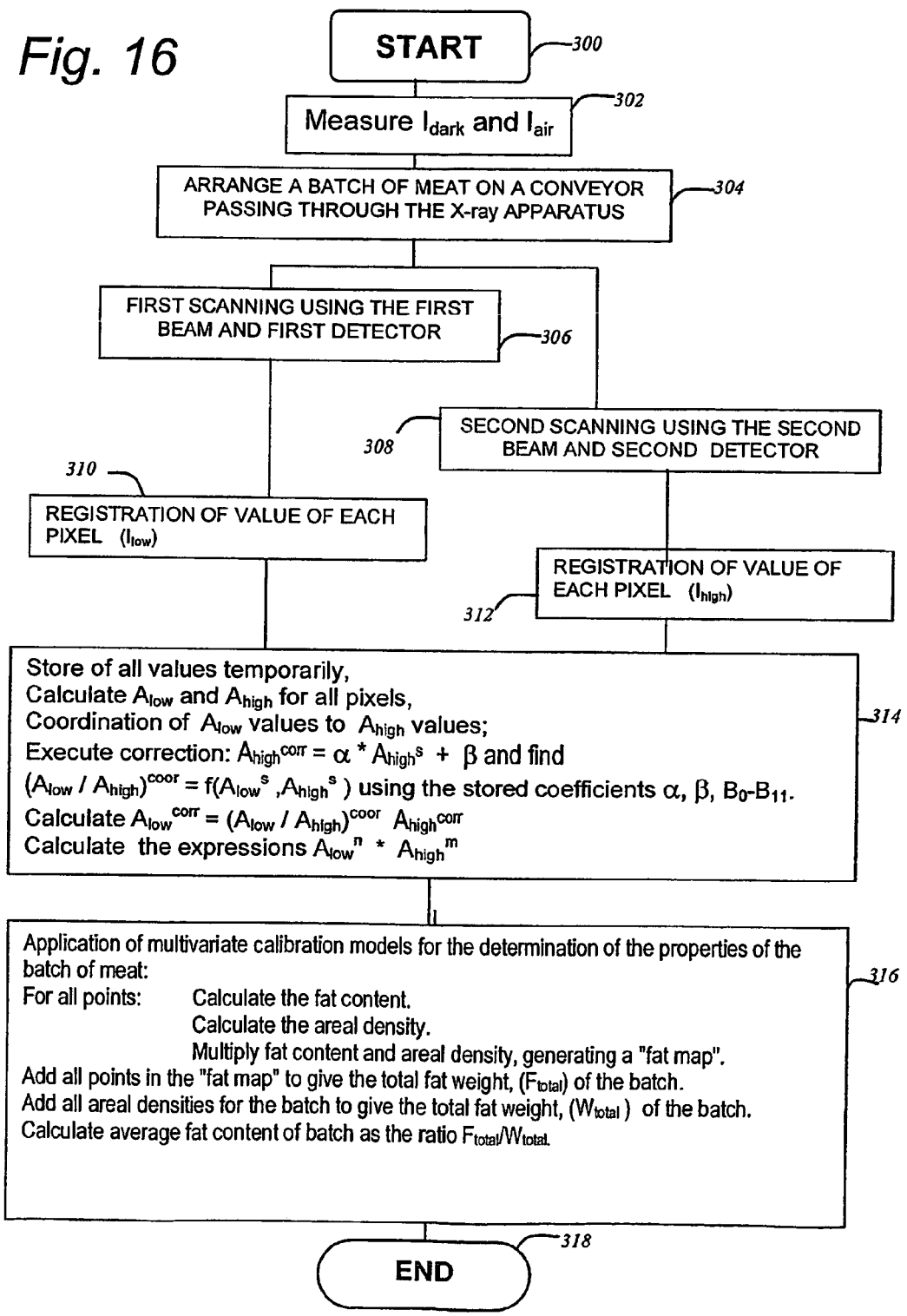
FIG. 16 shows a flow diagram illustrating the new measurement process using a standardized slave.

C. Measuring an Unknown Meat Sample on the Standardized Slave Instrument:

A presently preferred procedure for measuring a new meat sample on the slave instrument is illustrated in FIG. 16 where the steps 300, 302, 304, 306, 308, 310, 312, 316 and 318 are the same as the corresponding reference numbers mentioned before regarding FIG. 14. A container (FIG. 4) is arranged on the conveyor 10. During the passage through the instrument the two X-ray beams pass through the meat, container bottom, conveyor belt and reach the detectors 22, 24, generating signals representing the two images shown in FIGS. 5, 6. Data representing the intensities $I_{low}$, $I_{high}$ are stored temporarily. $I_{dark}$ and $I_{air}$ are measure regularly in step 312. Absorbances $A_{low}^S$, $A_{high}^S$ are calculated by use of formula (1a) and (1b). For each pixel-or alternatively a small group of neighboring pixels—two matching values $A_{low}^S$, $A_{high}^S$ are coordinated. So far the data treatment is the same as shown in FIG. 14. According to the present invention the following treatment is applied to the raw measurements, $A_{low}^S$ and $A_{high}^S$, from the slave instrument as shown in the steps listed in box 314:

1. The corrected high energy absorption, $A_{high}^{corr}$, is calculated:

$$A_{high}^{corr} = \alpha \cdot A_{high}^s + \beta$$

by using $\alpha$ and $\beta$ determined as disclosed above in section C.

2. The corrected absorption ratio, $[A_{low}/A_{high}]^{corr}$, is calculated:

$$\left[\frac{A_{low}}{A_{high}}\right]^{corr} = f(A_{low}^s, A_{high}^s)$$

where $f$ is the function defined above in section C.

3. The corrected low energy absorption, $A_{low}^{corr}$, is calculated:

$$\left[\frac{A_{low}}{A_{high}}\right]^{corr} = f(A_{low}^s, A_{high}^s)$$

These corrected absorbances, $A_{low}^{corr}$ and $A_{high}^{corr}$, are hereafter used for predictive purposes, e.g. prediction of the fat content of a meat sample using a calibration model generated on the master instrument (or any other instrument in the population of standardised instruments). This is indicated in the box 316, which is identical to box 116 in FIG. 14.

The example presented below shows how the method may work in practice.

Meat Samples used for Exemplifying the Method According to the Invention:

86 samples consisting of minced pork, turkey, and beef meat were prepared. These samples were frozen in blocks of varying heights (from 10 to 200 mm, corresponding to areal densities from 1 to 21 g/cm$^2$). The fat content of these samples was determined using the fat reference method (SBR, Schmid-Bondzynski-Ratzlaff). It ranged from 2 to 73%. 44 of these samples were used for building calibration models while the remaining 42 samples were used for independent testing of the standardisation method.

Description of the Measurements

The 26 artificial samples and the 86 meat samples were measured on equipment as described above. According to previous experience it is known that particularly voltage changes in the low X-ray sources cause serious problems with the transferability of the calibrations. Therefore, the experiment was carried out five times with different voltage settings of the two energy sources, on different instruments. The following settings were used:

Instrument 1 (master): $E_{low}$=62 kV, $E_{high}$=120 kV

Instrument 2 (slave): $E_{low}$=58 kV, $E_{high}$=100 kV

Instrument 3 (slave): $E_{low}$=58 kV, $E_{high}$=110 kV

Instrument 4 (slave): $E_{10}$=66 kV, $E_{high}$=110 kV

Instrument 5 (slave): $E_{low}$=66 kV, $E_{high}$=100 kV.

Use of the Method

PLS calibration models for fat and areal density based oh 44 meat samples were calculated on data from Instrument 1. This instrument is therefore regarded as the master instrument against which the so-called slave instruments (Instruments 2 to 5) will be evaluated. The calibration models consist of linear combinations of various ratios and products of $A_{low}$ and $A_{high}$, such that the fat % in a specific specific area or point of an object, above a specific single detection element, or alternatively a neighborhood of adjacent detection elements, such as four or nine, may be calculated as:

$$\text{Fat \%} = b_0 + b_1 * A_{low} + b_2 * A_{high} + b_3 * A_{low}^2 + b_4 * A_{high}^2 + b_5 A_{low}/A_{high} + b_6 * A_{low} * A_{high} + b_7 * A_{low}^2 * A_{high} + b_8 * A_{low} * A_{high}^2 + b_9 * A_{low}^2 * A_{high}^2 + b_{10} * A_{low}^2 * A_{high}^4 + b_{11} * A_{low}^2 / A_{high} + b_{12} * A_{low}/A_{high}^2 + b_{13} * A_{low}^2 / A_{high}^2 + b_{14} * A_{low}^3 / A_{high}^2 + b_{16} * A_{low}^4 / A_{high}^2 + b_{16} * 1/A_{high}^4 + b_{17} * A_{low}^4 / A_{high}^3 + b_{18} * A_{low}^3 / A_{high}^4 + b_{19} * A_{low}/A_{high}^4 + \ldots + b_p * A_{low}^{n1} / A_{high}^{m1}$$

wherein $b_0, b_1, \ldots b_p$ (some of them may be zero) are the calibration coefficients determined through multivariate calibration. Typically, the series is truncated so as to contain only term up to power two, such as power three, preferably power four of A.

It is contemplated that the expected accuracy of a calibrated instrument against the reference method (expressed as the Root Mean Square Error of Prediction, RMSEP) is better than 1% for the fat determination and approx 0.1 g/cm² for the areal density determination.

Figure 17:
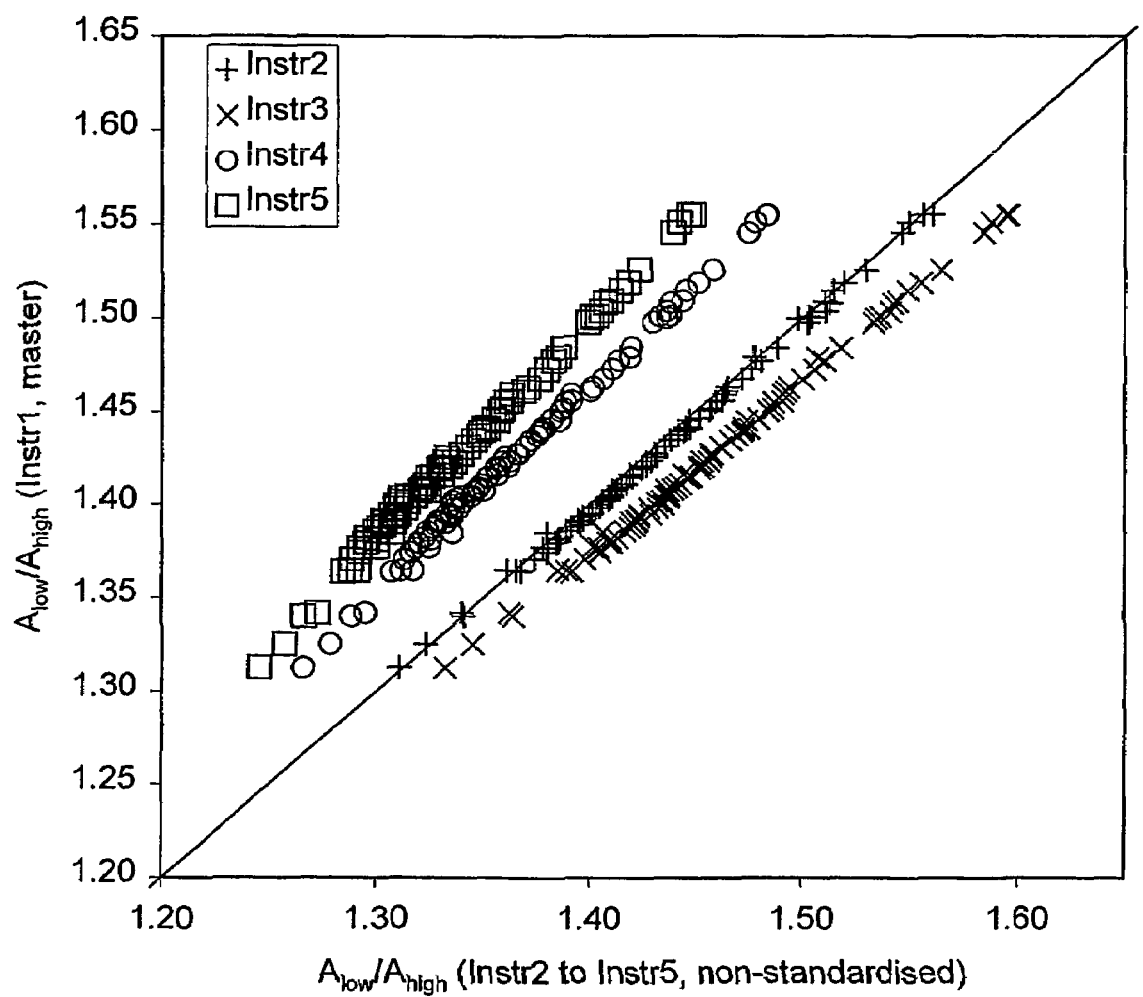
FIG. 17 shows a plot of ratios of non-standardised absorbances obtained with four non-standardised instruments against ratios of absorbances obtained with a master instrument.

The $A_{low}/A_{high}$ ratio is the parameter that is most sensitive to whether the instrument is standardised or not. This is of major importance, since this ratio is one of the major contributors to the calibration model for fat. In FIG. 17 this ratio for the 86 meat samples measured on the master instrument is plotted against the non-standardised ratios for the slave instruments. If no standardisation problems existed, the points should be close to the straight line indicated in the figure. This is, however, far from true: especially Instrument 5 shows large errors. A simple slope and intercept correction of this error will not help the problem completely, as the points, apart from showing a large systematic error, are also scattered along an imaginary line passing through the cloud of points. This is the reason why eleven or more terms are required in $f(A_{low}^s, A_{high}^s)$.

Figure 18:
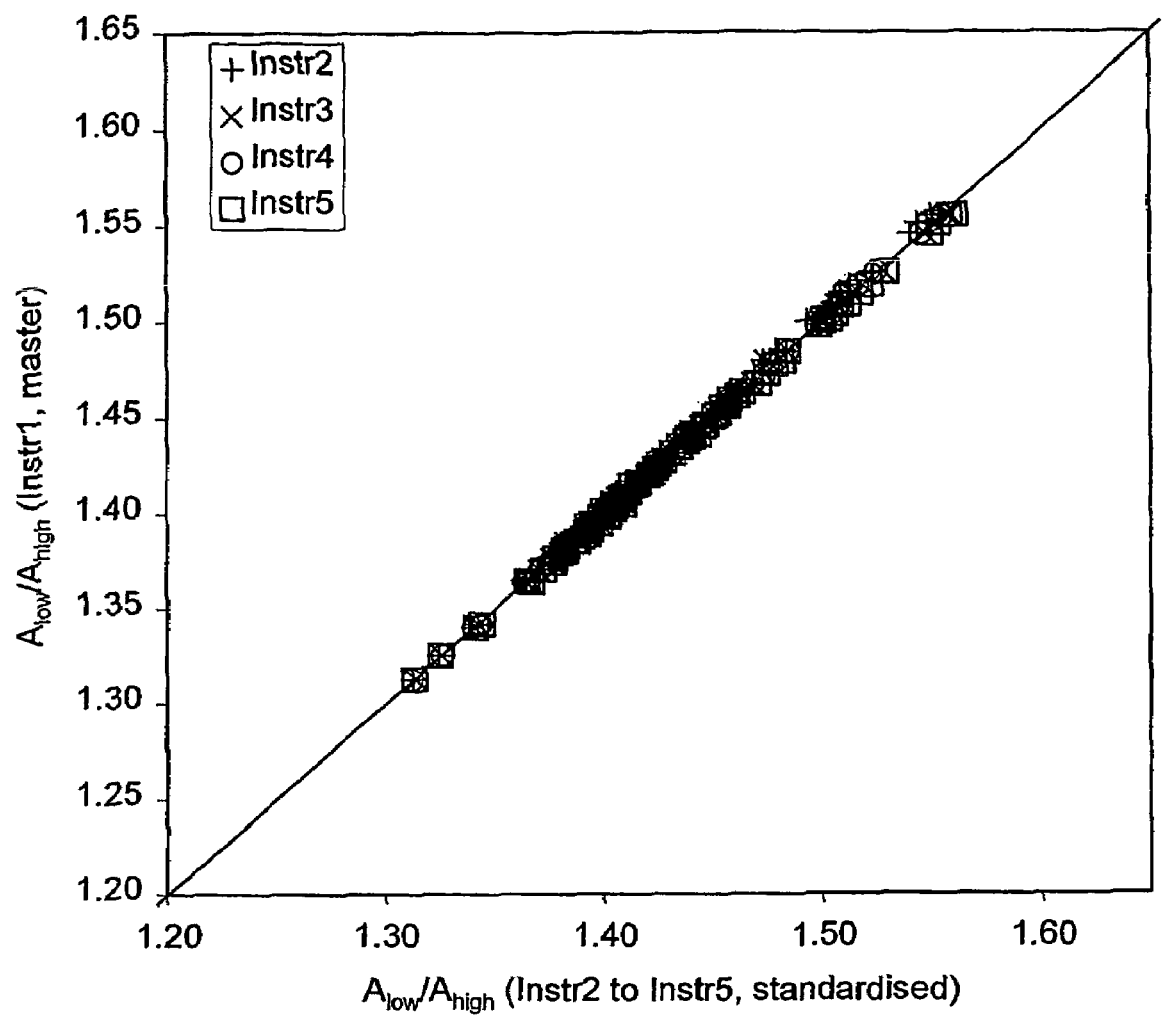
FIG. 18 shows a plot of ratios of standardised absorbances obtained with four standardised instruments against ratios of absorbances obtained with a master instrument.

After calculation of the Instrument dependent standardisation (correction) coefficients; $\alpha$, $\beta$, and $B_0$ to $B_{11}$, for Instrument 2 to 5 from the data obtained on the 26 artificial samples, the absorbances of the 86 meat samples were corrected using these coefficients. This resulted in a set of corrected ratios, $[A_{low}/A_{high}]^{corr}$, that are plotted in FIG. 18. The ratios are now very close to the line, indicating that the ratio is independent of the instrument from which it originated, which means that calibration models can be transferred between instruments.

The result of various attempts to use the calibration models based on data from the master (Instrument 1) are presented in Table A. Firstly, the calibration models for fat and areal density were applied to the raw, non-standardised data from the 42 independent test meat samples (corresponding to the data presented in FIG. 17). As is evident from column two and four of Table A, this results in very large and unacceptable prediction error. When standardisation is applied (corresponding to the data presented in FIG. 18), on the other hand, the prediction errors for the slaves (Instruments 2 to 5) cannot be distinguished from the prediction error for the master (Instrument 1). This can be seen in columns three and five of Table A.

TABLE A

The prediction error is stated in terms of the Root Mean Square Error of Prediction (RMSEP)

| Instrument | Non-standardised fat prediction error (%) | Standardised fat prediction error (%) | Non-standardised areal density prediction error (g/cm²) | Sandardised areal density prediction error (g/cm²) |
|---|---|---|---|---|
| 1 master | 0.66 | 0.66 | 0.10 | 0.10 |
| 2 slave | 4.56 | 1.06 | 0.43 | 0.12 |
| 3 slave | 20.89 | 0.90 | 0.32 | 0.12 |
| 4 slave | 38.08 | 0.72 | 0.19 | 0.11 |
| 5 slave | 54.07 | 1.15 | 0.09 | 0.11 |

Comments

The example given above thus shows the advantages of using the described method for standardising an X-ray instrument. The major advantage lies typically in the fact that it is possible to use stable artificial samples with well-defined absorption characteristics for obtaining standardised fat and areal density predictions instead of having to perform a labour intensive and expensive calibration procedure for every new instrument or every time an instrument is modified, e.g. by replacing a defect X-ray source or detector.

While a single particular embodiment of the invention has been mentioned, it will be understood, of course, that the invention is not limited thereto since many modifications may be made. It is contemplated that it will be useful for other kinds of electromagnetic radiation as well, e.g. Infrared light. It is, therefore, contemplated to cover by the appended claims any such modifications as fall within the true spirit and scope of the invention.

The invention claimed is:

1. A method of providing a correction for a slave instrument, the slave instrument measuring properties of an object by exposing the object to electromagnetic radiation in at least two spectral ranges and obtaining one or more object responses thereto, the responses being based on detecting at least one of attenuation, reflection and scattering of the electromagnetic radiation in or from the object by use of one or more detectors, the responses obtained in a form where they express properties either directly or via a transformation, said method of correction comprising:

obtaining, for a plurality of stable objects, a set of responses, comprising one or more pairs of related responses ($Q_{low}^S$ and $Q_{high}^S$), representing measurements in the at least two spectral ranges performed with the slave instrument and a set of responses, comprising one or more pairs of related responses ($Q_{low}^m$ and $Q_{high}^m$), representing measurements in the at least two spectral ranges performed with a master instrument;

wherein a pair of related responses ($Q_{low}^m$ and $Q_{high}^m$) of the master instrument corresponds to each pair of related responses ($Q_{low}^S$ and $Q_{high}^S$) of the slave instrument, wherein each element in the corresponding pair of responses ($Q_{low}^m$ and $Q_{high}^m$) of the master instrument corresponds to an element in each pair of responses ($Q_{low}^S$ and $Q_{high}^S$) of the slave instrument, determining, based on the sets of responses, a correcting function, the correcting function being a functional relationship between a ratio of related responses of the master instrument and a sum of a plurality of terms, each term being a product of a correcting coefficient ($B_i$) and powers of related responses ($Q_{low}^S$ and $Q_{high}^S$) of the slave instrument, wherein each response is raised to a power being a positive or negative real number, or zero, thereby determining a first set of correcting coefficients ($B_0; B_1; B_2 \ldots$);

storing the first set of correcting coefficients ($B_0; B_1; B_2 \ldots$) in a memory included in or adapted for communication with a data processing unit included in or adapted for communication with the slave instrument wherein the first set of correcting coefficients are used to provide a correction for the slave instrument;

initially measuring the plurality of stable objects on the master instrument to obtain the set of responses ($Q_{low}^m$ and $Q_{high}^m$) representing measurements performed with the master instrument; and initially storing the set of response ($Q_{low}^m$ and $Q_{high}^m$) initially measured as a set of constant values in the memory, the memory being accessible from the slave instrument when measuring the corresponding stable objects on a slave instrument.

2. The method according to claim 1, wherein the electromagnetic radiation comprises X-rays.

3. The method according to claim 1, wherein the determination of the correcting function is based on a regression method.

4. The method according to claim 3, wherein the regression method is selected from the group consisting of principal component regression, multiple linear regression, partial least squares regression, and artificial neural networks.

5. The method according to claim 1, wherein the correcting function comprises a plurality of terms of the following form: $Q_{low}^{n1} * Q_{high}^{m1}$, wherein n1 and m1 are selected from the group consisting of real numbers and integers, and n1 is positive.

6. The method according to claim 5, wherein the correcting function comprises at least three of the following terms: $Q_{low}, Q_{high}, Q_{low}^2, Q_{high}^2$ and $Q_{low}/Q_{high}$.

7. The method according to claim 5, wherein the correcting function comprises at least three of the following terms: $Q_{low} * Q_{high}; Q_{low}^2 * Q_{high}; Q_{low} * Q_{high}^2; Q_{low}^2/Q_{high}; Q_{low}/Q_{high}^2; Q_{low}^2/Q_{high}$; and $Q_{low}^2/Q_{high}^2$.

8. The method according to claim 1, wherein the correcting function is of the form:

$$\frac{Q_{low}^m}{Q_{high}^m} = B_1 Q_{low}^s + B_2 Q_{high}^s + B_3 Q_{low}^{s2} + B_4 Q_{high}^{s2} + B_5 Q_{low}^s Q_{high}^s + B_6 Q_{low}^{s2} Q_{high}^s + B_7 Q_{low}^s Q_{high}^{s2} + B_8 \frac{Q_{low}^s}{Q_{high}^s} + B_9 \frac{Q_{low}^{s2}}{Q_{high}^s} + B_{10} \frac{Q_{low}^s}{Q_{high}^{s2}} + B_{11} \left[\frac{Q_{low}^s}{Q_{high}^s}\right]^2 + B_0$$

wherein the Bs are constants.

9. The method according to claim 1, further comprising:
determining, based on the sets of responses, a further correcting function, being a functional relationship between responses of the slave instrument ($Q_{low}^S$ or $Q_{high}^S$) and related responses ($Q_{low}^m$ or $Q_{high}^m$) of the master instrument, thereby determining a second set of correcting coefficients, $\alpha$ and $\beta$.

10. The method according to claim 9, wherein the further correcting function is a functional relationship between a high energy response of the slave instrument ($Q_{high}^S$) and the related high energy response ($Q_{high}^m$) of the master instrument.

11. The method according to claim 10, wherein the further correcting function is determined by use of univariate linear regression.

12. The method according to claim 11, wherein the further correcting function is of the form $Q_{high}^m = \alpha \cdot Q_{high}^S + \beta$.

13. The method according to claim 1, wherein the set of responses for the master instrument and the set of responses for the slave instrument each comprise one pair of related responses for each stable object comprised in the plurality of stable objects.

14. The method according to claim 1, wherein the related responses are obtained based on measurements on objects being conveyed.

15. The method according to claim 1, wherein each of the responses (Q) is an intensity (I).

16. The method according to claim 1, wherein each of the responses (Q) is an intensity (I) corrected with respect to dark current of the detectors.

17. The method according to claim 1 wherein each of the responses is a transmittance (T) being a ratio between an intensity resulting from measuring an object and a reference intensity.

18. The method according to claim 1, wherein each of responses is an absorbance, A, being defined as the negative logarithm to a transmittance, T, (A=−log(T)).

19. The method according to claim 18, wherein the logarithm is one of a logarithm base 10 and a natural logarithm.

20. The method according to claim 1, wherein the responses for both the master and the slave instruments are absorbances, $A_{low}$ and $A_{high}$, being determined by calculating $$A_{low} = -\log_{10}\left[\frac{I_{sample}(\text{low}) - I_{dark}(\text{low})}{I_{air}(\text{low}) - I_{dark}(\text{low})}\right] \text{ and}$$

$$A_{low} = -\log_{10}\left[\frac{I_{sample}(\text{high}) - I_{dark}(\text{high})}{I_{air}(\text{high}) - I_{dark}(\text{high})}\right]$$

wherein $I_{sample}$ is the intensity of the radiation detected when the object is irradiated, $I_{dark}$ is the intensity of the radiation detected when the object is not irradiated, and $I_{air}$ is the intensity of the radiation detected when no object is present, the intensities obtained in a measuring region in respective of the master instrument and the slave instrument by:

exposing the object in the measuring region to low and high X-ray energies and detecting with detectors the intensities $I_{sample}$(low) and $I_{sample}$(high), respectively;

detecting the intensities $I_{dark}$(low) and $I_{dark}$(high) from said detectors when no radiation reaches them; and exposing said detectors to the low and high X-ray energies when no object is present in the measuring region and detecting $I_{air}$(low) and $I_{air}$(high), respectively.

21. The method according to claim 1, wherein each of the responses is a reflectance (R) expressing the reflectance from the surface of a respective of the objects.

22. The method according to claim 21, wherein the reflectance (R) is linearized, using the Kubelka-Munk transform (K/S=(1−R)/2R).

23. A method of correcting responses representing measurements for an object performed with a slave instrument, said method comprising:

determining, based on measurements with the slave instrument, a pair of related responses ($Q_{low}^S$ and $Q_{high}^S$);

determining a ratio $[Q_{low}/Q_{high}]^{corr}$ using a correcting function, the correcting function being a functional relationship between a ratio of a pair of related responses ($Q_{low}^m$ and $Q_{high}^m$) of a master instrument and a sum of a plurality of terms, each term of the plurality of terms being a product of a correcting coefficient ($B_i$) and powers of related responses ($Q_{low}^S$ and $Q_{high}^S$) of the slave instrument, wherein each response is raised to a power being a positive or negative real number, or zero;

providing $Q_{high}^{corr}$, where $Q_{high}^{corr}$ is substantially equal to $Q_{high}^S$, or $Q_{high}^{corr}$ is determined using a further correcting function correlating $Q_{high}^{corr}$ with $Q_{high}^S$;

calculating $Q_{low}^{corr}$ as equal to $Q_{high}^{corr} * [Q_{low}/Q_{high}]^{corr}$, and thereby providing a set of corrected responses;

initially measuring a plurality of stable objects on the master instrument to obtain the pair of related responses to ($Q_{low}^m$ and $Q_{high}^m$) representing measurements performed with the master instrument; and initially storing the pair of related response ($Q_{low}^m$ and $Q_{high}^m$) initially measured as a set of constant values in a memory, the memory being accessible from the slave instrument when measuring the corresponding stable objects on a slave instrument.

24. The method according to claim 23, wherein the further correcting function is of the form: $Q_{high}^{corr} = \alpha \cdot Q_{high}^S + \beta$.

25. The method according to claim 23, wherein the correcting function comprises terms of the following form: $Q_{low}^{n1} * Q_{high}^{m1}$, wherein n1 and m1 are one of real numbers and integers, and wherein n1 is positive.

26. The method according to claim 23, wherein the correcting function comprises at least three of the following terms: $Q_{low}$, $Q_{high}$, $Q_{low}^2$, $Q_{high}^2$ and $Q_{low}/Q_{high}$.

27. The method according to claim 23, wherein the correcting function comprising at least three of the following terms: $Q_{low}*Q_{high}$; $Q_{low}^2*Q_{high}$; $Q_{low}*Q_{high}^2$; $Q_{low}^2/Q_{high}$; $Q_{low}/Q_{high}^2$; $Q_{low}^2/Q_{high}^2$; and $Q_{low}^2/Q_{high}^2$.

28. The method according to claim 23, wherein the correcting function is of the form:

29. The method according to claim 23, wherein each of the responses (Q) is an intensity (I).

30. The method according to claim 23, wherein each of the responses (Q) is an intensity (I) corrected with respect to dark current of the detectors.

31. The method according to claim 23, wherein each of the responses is a transmittance (T) being a ratio between intensity resulting from measuring an object and a reference intensity.

32. The method according to claim 23, wherein each of responses is an absorbance, A, defined as the negative logarithm to a transmittance, T, (A=−log(T)).

33. The method according to claim 32, wherein the logarithm is one of a logarithm base 10, and a natural logarithm.

34. The method according to claim 23, wherein the responses are absorbances being determined by calculating $$A_{low} = -\log_{10}\left[\frac{I_{sample}(\text{low}) - I_{dark}(\text{low})}{I_{air}(\text{low}) - I_{dark}(\text{low})}\right] \text{ and}$$

$$A_{high} = -\log_{10}\left[\frac{I_{sample}(\text{high}) - I_{dark}(\text{high})}{I_{air}(\text{high}) - I_{dark}(\text{high})}\right]$$

wherein $I_{sample}$ is the intensity of the radiation detected when the object is irradiated, $I_{dark}$ is the intensity of the radiation detected when the object is not irradiated, and $I_{air}$ is the intensity of the radiation detected when no object is present, the intensities obtained in a measuring region of the slave instrument by:

exposing an object in the measuring region to low and high X-ray energies and detecting with detectors the intensities $I_{sample}$(low) and $I_{sample}$(high), respectively;

detecting with the detectors the intensities $I_{dark}$(low)) and $I_{dark}$(high) from said detectors when no radiation reaches them; and exposing said detectors to the low and high X-ray energies when no object is present in the measuring region and detecting $I_{air}$(low) and $I_{air}$(high), respectively.

35. The method according to claim 23, wherein each of the responses is a reflectance (R) expressing the reflectance from the surface of a respective of the objects.

36. The method according to claim 35, wherein the reflectance (R) is linearized using the Kubelka-Munk transform (K/S=(1−R)/2R).

37. A method of determining a physical quantity for an object by a slave instrument, the method comprising:

determining for the object corrected high and low energy responses ($Q_{high}^{corr}$ and $Q_{low}^{corr}$) using the method according to claim 23; and determining the physical quantity by applying a calibrated functional relationship between $Q_{high}^{corr}$ and $Q_{low}^{corr}$ and a physical quantity on said corrected responses.

38. The method according to claim 37, wherein the calibration model is obtained by exposing the master instrument to a plurality of well-defined objects.

$$\left[\frac{Q_{low}}{Q_{high}}\right]^{corr} = B_1 Q_{low}^s + B_2 Q_{high}^s + B_2 Q_{low}^{s2} + B_4 Q_{high}^{s2} + B_5 Q_{low}^s Q_{high}^s +$$

$$B_6 Q_{low}^{s2} Q_{high}^s + B_7 Q_{low}^s Q_{high}^{s2} + B_8 \frac{Q_{low}^s}{Q_{high}^s} + B_9 \frac{Q_{low}^{s2}}{Q_{high}^s} + B_{10} \frac{Q_{low}^s}{Q_{high}^s} + B_{11}\left[\frac{Q_{low}^s}{Q_{high}^s}\right]^2 + B_0$$

wherein the Bs are constants.

39. The method according to claim 38, wherein the well-defined objects are defined such that physical properties of the objects have been established by a chemical process.

40. The method according to claim 39, wherein the chemical process is a reference method for the determination of the physical properties.

41. The method according to claim 37, wherein each of the responses (Q) is one of:
- an intensity (I);
- a transmittance (T) derived as a ratio between intensity resulting from measuring an object and a reference intensity;
- an absorbance defined as the negative logarithm to a transmittance ($A=-\log(T)$); and
- a reflectance (R) expressing the reflectance from the surface of an object, the reflectance (R) being linearized using the Kubelka-Munk transform ($K/S(1-R)/2R$).

42. The method according to claim 41, wherein, the responses are absorbances, the absorbances being determined by calculating $$A_{low} = -\log_{10}\left[\frac{I_{sample}(low) - I_{dark}(low)}{I_{air}(low) - I_{dark}(low)}\right] \text{ and}$$

$$A_{high} = -\log_{10}\left[\frac{I_{sample}(high) - I_{dark}(high)}{I_{air}(high) - I_{dark}(high)}\right]$$

wherein $I_{sample}$ is the intensity of the radiation detected when the object is irradiated, $I_{dark}$ is the intensity of the radiation detected when the object is not irradiated, and $I_{air}$ is the intensity of the radiation detected when no object is present, the intensities obtained in a measuring region of the slave instrument by:
- exposing an object in the measuring region to low and high X-ray energies and detecting with detectors the intensities $I_{sample}(low)$ and $I_{sample}(high)$, respectively;
- detecting with the detectors the intensities $I_{dark}(low)$ and $I_{dark}(high)$ from said detectors when no radiation reaches them; and
- exposing said detectors to the low and high X-ray energies when no object is present in the measuring region and detecting $I_{air}(low)$ and $I_{air}(high)$, respectively.

43. A method of determining a physical quantity for an object by a slave instrument, the method comprising:
- determining for the object corrected high and low energy responses ($Q_{high}^{corr}$ and $Q_{low}^{corr}$) using the method according to claim 23; and
- determining the physical quantity by applying a calibrated functional relationship between $Q_{high}^{corr}$ and $Q_{low}^{corr}$ and a physical quantity on said corrected responses,
- wherein the calibrated functional relationship is a functional relationship between a physical quantity and a sum of a plurality of terms, each term being a product of a calibration coefficient ($B_i$) and powers of related responses ($Q_{low}^S$ and $Q_{high}^S$), wherein each response is raised to a power being a positive or negative real number, or zero.

44. The method according to claim 43, wherein the calibrated functional relationship comprises terms of the form: $Q_{low}^{n1} * Q_{high}^{m1}$, wherein n1 and m1 are at least one of real numbers and integers, and wherein n1 is positive.

45. The method according to claim 44, wherein the calibrated functional relationship comprises terms of the form: $Q_{low} * Q_{high}$; $Q_{low}^2$, $Q_{high}^2$ and $Q_{low}/Q_{high}$.

46. The method according to claim 44, wherein the calibrated functional relationship comprises terms of the form: $Q_{low} * Q_{high}$; $Q_{low}^2 * Q_{high}$; $Q_{low} * Q_{high}^2$, $Q_{low}^2/Q_{high}$; $Q_{low}/Q_{high}^2$; $Q_{low}^2/Q_{high}^2$; and $Q_{low}^2/Q_{high}^2$.

47. The method according to claim 44, wherein the calibrated functional relationship is of the form:

$$F(Q) = B_1 Q_{low}^{s2} + B_2 Q_{high}^{s} + B_3 Q_{low}^{s2} + B_4 Q_{high}^{s2} + B_5 Q_{low}^{s} Q_{high}^{s} + B_6 Q_{low}^{s2} Q_{high}^{s} + B_7 Q_{low}^{s} Q_{high}^{s2} + B_8 \frac{Q_{low}^{s}}{Q_{high}^{s}} + B_9 \frac{Q_{low}^{s2}}{Q_{high}^{s}} + B_{10} \frac{Q_{low}^{s}}{Q_{high}^{s2}} + B_{11}\left[\frac{Q_{low}^{s}}{Q_{high}^{s}}\right] + B_0$$

wherein the Bs are constants.

48. A method of using a slave instrument for determining physical quantities of an object by use of dual X-ray radiation, the method comprising:
- scanning substantially all or all of the object using X-ray beams having at least two energy levels, the at least two energy levels including a low energy level and a high energy level, the high energy level being higher relatively to the low energy level;
- detecting the X-ray beams having passed through the object for a plurality of areas of the object;
- determining, for each area of the object, the object's response ($Q_{low}$) at the low energy level and the object's response ($Q_{high}$) at the high energy level;
- correcting the responses so determined using the correcting method according to claim 24; and
- determining the physical quantity by applying a calibrated functional relationship between $Q_{high}^{corr}$ and $Q_{low}^{corr}$ and a physical quantity on said corrected responses.

49. The method according to claim 48, wherein the physical quantity is fat content.

50. The method according to claim 48, wherein the object is at least one of food and feed.

51. A correcting system comprising a slave instrument for obtaining responses and a data processing system for correcting the responses, the responses representing measurements performed with the slave instrument and the responses based on detecting by the slave instrument at least one of attenuation, reflection and scattering of electromagnetic radiation in or from an object exposed to said electromagnetic radiation in at least two spectral ranges, the set of responses comprises one or more pairs of related responses ($Q_{low}^S$ and $Q_{high}^S$), said correcting system comprising:
- a first processor means for determining the one or more pairs of related responses ($Q_{low}^S$ and $Q_{high}^S$) based on measurements on an object with the slave instrument;
- a second processor means for performing a correction of responses using a correction according to claim 23, said second processor means comprising an accessing unit configured to access a memory storing a first set of correction coefficients ($B_0$; $B_1$; $B_2$ ...);
- a third processor means for determining the ratio $[Q_{low}/Q_{high}]^{corr}$ by the correcting function;
- a fourth processor means for determining the corrected high energy response $Q_{high}^{corr}$ by the further correcting function; and
- a fifth processor means for determining the corrected low energy response $Q_{low}^{corr}$ by multiplying $[Q_{low}/Q_{high}]^{corr}$ by $Q_{high}^{corr}$.

52. The system according to claim 51, wherein the electromagnetic radiation comprises x-rays.

53. The system according to claim 51, wherein each of the responses (Q) is one of:
- an intensity (I);
- a transmittance (T) derived from intensity as a ratio between intensity resulting from measuring an object and a reference intensity;
- an absorbance, A, being defined as the negative logarithm to a transmittance, T, (A=−log(T)); and
- a reflectance (R) expressing the reflectance from the surface of an object, the reflectance (R) being linearized using the Kubelka-Munk transform (K/S=(1−R)/2R).

54. A data processing system for providing a correction for a slave instrument, said system using sets of responses based on detecting at least one of attenuation, reflection and scattering of electromagnetic radiation in or from an object exposed to said electromagnetic radiation in at least two spectral ranges, the set of responses comprising one or more pairs of related responses ($Q_{low}^S$ and $Q_{high}^S$) representing measurements performed with the slave instrument and a set of responses comprising one or more pairs of related responses ($Q_{low}^m$ and $Q_{high}^m$) representing measurements having initially been performed with a master instrument, said responses being obtained for a plurality of stable objects, wherein each pair of related responses of the master instrument corresponds to a respective pair of related responses of the slave instrument, wherein each element in the corresponding pair of responses of the master instrument corresponds to a respective element in each pair of responses of the slave instrument, said data processing system comprising:
- an accessing unit configured to access a memory, wherein the responses ($Q_{low}^m$ and $Q_{high}^m$) of the master instrument and/or the responses ($Q_{low}^S$ and $Q_{high}^S$) of the slave instrument are stored;
- a processor configured to determine, based on the sets of responses, a correcting function, the correcting function being a functional relationship between a ratio of related responses of the master instrument and a sum of a plurality of terms, each term being a product of a correcting coefficient ($B_i$) and powers of related responses ($Q_{low}^S$ and $Q_{high}^S$) of the slave instrument wherein each response is raised to a power being a positive or negative real number, or zero, thereby determining a first set of correcting coefficients ($B_0$; $B_1$; $B_2$ . . . );
- a storage unit configured to store the first set of correction coefficients ($B_0$; $B_1$; $B_2$ . . . ); and
- a memory holding the pair of related response ($Q_{low}^m$ and $Q_{high}^m$), representing the measurements having been initially performed with the master instrument, as a set of constant values, the memory being accessible from the slave instrument when measuring the corresponding stable objects on the slave instrument.

55. The data processing system according to claim 54, wherein the electromagnetic radiation comprises X-rays.

56. The data processing system according to claim 54, further comprising:
- a processor configured to determine a further correcting function, the further correcting function being a functional relationship between a high energy response of the slave instrument ($Q_{high}^S$) and related high energy response ($Q_{high}^m$) of the master instrument, thereby determining a second set of correcting coefficients, α and β.

57. The data processing system according to claim 54, wherein each of the responses (Q) is one of:
- an intensity (I);
- a transmittance (T) derived from intensity as a ratio between intensity resulting from measuring an object and a reference intensity;
- an absorbance, A, being defined as the negative logarithm to a transmittance, T, (A=−log(T)); and
- a reflectance (R) expressing the reflectance from the surface of an object, the reflectance (R) being linearized using the Kubelka-Munk transform (K/S=(1−R)/2R).

58. A data processing system according to claim 57, wherein the responses are absorbances, the absorbances being determined by calculating $$A_{low} = -\log_{10}\left[\frac{I_{sample}(\text{low}) - I_{dark}(\text{low})}{I_{air}(\text{low}) - I_{dark}(\text{low})}\right] \text{ and}$$

$$A_{low} = -\log_{10}\left[\frac{I_{sample}(\text{high}) - I_{dark}(\text{high})}{I_{air}(\text{high}) - I_{dark}(\text{high})}\right]$$

wherein $I_{sample}$ is the intensity of the radiation detected when the object is irradiated, $I_{dark}$ is the intensity of the radiation detected when the object is not irradiated, and $I_{air}$ is the intensity of the radiation detected when no object is present, the intensities obtained in a measuring region of the slave instrument by:
- exposing an object in the measuring region to low and high X-ray energies and detecting with detectors the intensities $I_{sample}$(low) and $I_{sample}$(high), respectively;
- detecting with the detectors the intensities $I_{dark}$(low) and $I_{dark}$(high) from said detectors when no radiation reaches them; and
- exposing said detectors to the low and high X-ray energies when no object is present in the measuring region and detecting $I_{air}$(low) and $I_{air}$(high), respectively.

59. The system according to claim 54, further comprising:
- a storage unit configured to store at least one of: a set of responses ($Q_{low}^m$ and $Q_{high}^m$) for the set of stable objects measured on the master instrument, the first set of correction coefficients ($B_0$; $B_1$; $B_2$ . . . ), and the further correcting function.

60. A method of providing a correction for a slave instrument, the slave instrument measuring properties of an object by exposing the object to electromagnetic radiation in at least two spectral ranges and obtaining one or more object responses thereto, the responses being based on detecting at least one of attenuation, reflection and scattering of the electromagnetic radiation in or from the object by use of one or more detectors, the responses obtained in a form where they express properties either directly or via a transformation, said method of correction comprising:
- (A) obtaining, for a plurality of stable objects, a set of responses, comprising one or more pairs of related responses ($Q_{low}^S$ and $Q_{high}^S$), representing measurements in the at least two spectral ranges performed with the slave instrument and a set of responses, comprising one or more pairs of related responses ($Q_{low}^m$ and $Q_{high}^m$), representing measurements in the at least two spectral ranges performed with a master instrument, each stable object comprising at least a first and second different chemical compositions which are substantially stable, the first chemical compositions having X-ray response properties similar to adipose tissue, and the second chemical compositions having X-ray response properties similar to muscle tissue, wherein (i) a pair of related responses ($Q_{low}^m$ and $Q_{high}^m$) of the master instrument corresponds to each pair of related responses ($Q_{low}^S$ and $Q_{high}^S$) of the slave instrument and
(ii) each element in the corresponding pair of responses ($Q_{low}^m$ and $Q_{high}^m$) of the master instrument corresponds to an element in each pair of responses ($Q_{low}^S$ and $Q_{high}^S$) of the slave instrument;

(B) determining, based on the sets of responses, a correcting function, the correcting function being a functional relationship between a ratio of related responses of the master instrument and a sum of a plurality of terms, each term being a product of a correcting coefficient ($B_i$) and powers of related responses ($Q_{low}^S$ and $Q_{high}^S$) of the slave instrument, wherein each response is raised to a power being a positive or negative real number, or zero, thereby determining a first set of correcting coefficients ($B_0$; $B_1$; $B_2$ . . . ); and (C) storing the first set of correcting coefficients ($B_0$; $B_1$; $B_2$ . . . ) in a memory means included in or adapted for communication with a data processing unit included in or adapted for communication with the slave instrument, wherein the first set of correcting coefficients are used to provide a correction for the slave instrument.

\* \* \* \* \*